US007947308B2

(12) United States Patent
Loebenberg et al.

(10) Patent No.: US 7,947,308 B2
(45) Date of Patent: May 24, 2011

(54) EFFERVESCENT POWDERS FOR INHALATION

(76) Inventors: Raimar Loebenberg, Edmonton (CA); Warren H. Finlay, Edmonton (CA); Wilson H. Roa, Edmonton (CA); Leticia Ely, Edmonton (CA)

( * ) Notice: Subject to any disclaimer, the term of this patent is extended or adjusted under 35 U.S.C. 154(b) by 1251 days.

(21) Appl. No.: 11/490,331

(22) Filed: Jul. 20, 2006

(65) Prior Publication Data

US 2007/0031490 A1 Feb. 8, 2007

Related U.S. Application Data

(60) Provisional application No. 60/700,734, filed on Jul. 20, 2005.

(51) Int. Cl.

| | |
|---|---|
| ***A61K 9/14*** | (2006.01) |
| ***A61K 9/00*** | (2006.01) |
| ***A61K 31/70*** | (2006.01) |
| ***A61K 31/7024*** | (2006.01) |
| ***A61K 31/47*** | (2006.01) |
| ***A61K 31/4709*** | (2006.01) |
| ***A61K 31/473*** | (2006.01) |
| ***A61K 47/00*** | (2006.01) |

(52) U.S. Cl. ............ 424/489; 424/46; 514/34; 514/312; 514/777; 514/784; 977/773

(58) Field of Classification Search .................... 424/46, 424/489; 514/34, 312, 777, 784

See application file for complete search history.

(56) References Cited

U.S. PATENT DOCUMENTS

| | | | | |
|---|---|---|---|---|
| 5,192,528 | A * | 3/1993 | Radhakrishnan et al. | 424/45 |
| 6,683,043 | B1 * | 1/2004 | Dovey et al. | 510/444 |
| 2002/0020412 | A1 * | 2/2002 | Gilbert et al. | 128/203.12 |
| 2004/0107963 | A1 | 6/2004 | Finlay et al. | 128/203.15 |
| 2005/0124663 | A1 * | 6/2005 | Gatlin et al. | 514/340 |
| 2006/0112958 | A1 * | 6/2006 | Fisher et al. | 128/203.16 |
| 2009/0181100 | A1 * | 7/2009 | Bosch et al. | 424/489 |

OTHER PUBLICATIONS

Hershey et al. "Inhalation Chemotherapy for Macroscopic Primary or Metastatic Lung Tumors: Proof of Principle Using Dogs with Spontaneously Occurring Tumors as a Model," Clinical Cancer Research, 1999, vol. 5, pp. 2653-2639.*

Merck Index, 10th edition, entry 3435, Merck & Co., Inc.: Rahway, NJ, 1983, pp. 499.*

Abraxane [prescribing information]. Schaumburg, III: Abraxis Oncology, a Division of American Pharmaceutical Partners, Inc; Jan. 2005.

Bosquillon, C. et al., "Influence of formulation excipients and physical characteristics of inhalation dry powders on their aerolization performance," *Journal of Controlled Release*, 2001, 70, 329-339.

Bosquillon, C. et al., "Pulmonary delivery of growth hormone using dry powders and visulization of its local fate in rats," *Journal of Controlled Release*, 2004, 96, 233-244.

Codrons, V. et al., "Systemic delivery of parathyroid hormone (1-34) using inhalation dry powder in rats," *Journal of Pharmaceutical Sciences*, 2003, 92(5), 938-950.

Corrigan, D. O. et al., "The effect of spray drying solutions of polyethylene glycol (PEG) and lactose/PEG on their physicochemical properties," *International J. of Pharmaceutics*, 2002, 235, 193-205.

Dailey, L. A., et al., "Nebulization of biodegradable nanoparticles: impact of nebulizer technology and nanoparticle characteristics on aerosol features," *Journal of Controlled Release*, 2003, 86, 131-144.

Davies, N. M. et al., "A novel method for assessing dissolution of aerosol inhaler products," *International Journal of Pharmaceutics*, 2003, 255, 175-87.

Edwards, D. A. et al., "Recent advances in pulmonary drug delivery using large, porous inhaled particles," *J Appl Physiol*, 1998, 85, 379-385.

Eichman, J. D. et al., "Mechanistic studies on effervescent—induced permeability enhancement," *Pharmaceutical Research*, 1998, 15(6), 925-930.

El-Shaboury, M. H. et al., "Effect of effervescent salt on the dissolution and bioavailability of drugs from capsules filled on a dosator-type capsule-filling machine," *Pharmazeutische Industrie*, 1993, 55(2), 176-179.

Elversson, J. et al., "Droplet and Particle Size Relationship and Shell Thickness of Inhalable Lactose Particles during Spray Drying," *Journal of Pharmaceutical Sciences*, 2002, 92(4), 900-910.

Garcia-Contreras, L. et al., "Pharmaceutical and biotechnological aerosols for cystic fibrosis therapy," *Advanced Drug Delivery Reviews*, 2002, 54, 1491-1504.

Gilani, K. et al., "Aerolization of beclomethasone diprionate using spray dried lactose/polyethylene glycol carriers," *European J. of Pharmaceutics and Biopharmaceutics*, 2004, 58, 596-606.

Gliński, J. et al., "Surface properties of aqueous solutions of L-leucine," *Biophysical Chemistry*, 2000, 84, 99-103.

Grenha, S. B. et al., "Microencapsulated chitosan nanoparticles for lung protein delivery," *European Journal of Pharmaceutical Sciences*, 2005, 25, 427-437.

Hardy, J. G. et al., "Sustained Release Drug Delivery to the lungs," *Clin Pharmacokinet*, 2000, 39, 1-4.

Karhu, M. et al., "Pulmonary deposition of lactose carrier used in inhalation powders," *International J. of Pharmaceutics*, 2000, 196, 95-103.

King, M. et al., "Clearance of mucus by simulated cough," *J. Appl. Physiol.*, 1985, 58(6), 1776-1782.

Kreuter, J., "Nanoparticle-based dmg delivery systems," *Journal of Controlled Release*, 1991, 16, 169-176.

(Continued)

*Primary Examiner* — James H Alstrum Acevedo

(74) *Attorney, Agent, or Firm* — Anthony R. Lambert

(57) ABSTRACT

Effervescent powders comprising inhalable particles are disclosed, as are methods for preparing these powders. The inhalable carrier particles comprise an inorganic or organic carbonate, and an acid, and exhibit effervescence when exposed to water or humid air. The particles have a mass median aerodynamic diameter suitable for nasal, bronchial, or pulmonary administration. The inhalable particles may be used as carriers for active agents. The inhalable particles may also be used to enhance permeability of mucosal and surface barriers on an inner surface of the nose, mouth, airway, and/or lungs of a patient, as well as to loosen, thin, cleanse, and remove mucus and extrinsic surface materials from an inner surface of the nose, mouth, airway, and/or lungs of a patient in need thereof.

18 Claims, 15 Drawing Sheets

OTHER PUBLICATIONS

Labiris, N. R. et al., "Pulmonary Drug Delivery. Part I: Physiological factors affecting therapeutic effectiveness of aerosolized medications," *Journal Clin Pharmacol.*, 2003, 56, 588-599.

Lucas, P. et al., "Enhancement of small particles size dry powder aerosol formulations using an ultra low-density additive," *Pharmaceutical Research*, 1999, 16(10), 1643-1647.

Oberdörster, G. et al., "An Emerging Discipline Evolving from Studies of Ultrafine Particles," *Environmental Health Perspectives*, 2005, 113(7), 823-839.

Pandey, R. et al., "Antitubercular inhaled therapy: opportunities, progress and challenges," *The Journal of Antimicrobial Chemotherapy*, 2005, 55(4), 430-435.

Petersen, F. J. et al., "Design and Atomization Properties for an Inside-Out Type Effervescent Atomizer," *Drug Development and Industrial Pharmacy*, 2004, 30(3), 319-326.

Rabbani, N. R. et al., "The influence of formulation components on the aerolization properties of spray dried powders," *J of Controlled Release*, 2005, 110, 130-140.

Rao, R. D. et al., "Aerosol Therapy for Malignancy Involving the Lungs," *Current Cancer Drug Targets*, 2003, 3(4), 239-250.

Rotthauser, B. et al., "Optimization of an effervescent tablet formulation containing spray dried L-Leucine and polyethylene glycol 6000 as lubrificants using a central composite design," *European Journal of Pharmaceutics and Biopharmaceutics*, 1998, 46, 85-94.

Rygnestad, T. et al., "Absorption of effervescent paracetamol tablets relative to ordinary paracetamol tablets in healthy volunteers," *European Journal of Clinical Pharmacology*, 2000, 56(2), 141-143.

Schúrch, S. et al., "Particles at the airway interfaces of the lung," *Colloids and surfaces B: Biointerfaces*, 1999, 15, 339-353.

Sham, J.-H. et al., "Formulation and characterization of spray—dried powders containing nanoparticles for aerosol delivery to the lung," *International Journal of Pharmaceutics*, 2004, 269, 457-467.

Sommerfeld, P. et al., "Sterilization of unloaded polybutylcyanoacrylate nanoparticles," *International Journal of Pharmaceutics*, 1998, 164, 113-118.

Steckel, H. et al., "A novel spray—drying technique to produce low density particles for pulmonary delivery," *International Journal of Pharmaceutics*, 2004, 278, 187-95.

Suarez, S. et al., "Airways delivery of rifampicin microparticles for the treatment of tuberculosis," *Journal of Antimicrobial Chemeotherapy*, 2001, 48, 431-434.

Tsapis, N. et al., "Trojan particles: Large porous carrier of nanoparticles for drug delivery," *Proc. Natl. Acad. Sci.*, 2002, 99, 12001-12005.

Vanbever, R. et al., "Formulation and Physical Characterization of Large Porous Particles for Inhalation," *Pharmaceutical Research*, 1999, 16(11), 1735-1742.

Voss, A. et al., "Degglomeration of dry powder pharmaceutical aerosols," *International Journal of Pharmaceutics*, 2002, 248, 39-50.

Wang, Z. et al., "A Dry Powder Inhaler with Reduced Mouth-throat Deposition," *J. Aerosol Med.*, 2006, 19(2) 168-174.

Zahoor, A. et al., "Inhalable alginate nanoparticles as antitubecular drug carriers against experimental tuberculosis," *International Journal of Antimicrobial Agents*, 2005, 26, 298-303.

* cited by examiner

Distribution of the nano particles in the gas bubble (A) and dissolving of the carrier after contact with humidity (B)

A) green channel
B) red channel
C) normal light
D) superimposed

A) 1.2 % lactose B) 2.4% lactose C) 3.5% lactose D) 10% lactose

A) B)

Body weight of mice (n=5) treated with 1mg effervescent powder containing nanoparticles.

Morbidity score of mice (n=5) treated with 1mg effervescent powder containing nanoparticles.

EFFERVESCENT POWDERS FOR INHALATION

This application claims priority from U.S. Provisional Application Ser. No. 60/700,734, filed Jul. 20, 2005.

FIELD OF THE INVENTION

The present invention relates to inhalable effervescent powders. More particularly, the invention relates to inhalable effervescent powders containing particles suitable for nasal, bronchial, and pulmonary administration. These particles may act as carriers for delivery of active agents such as therapeutic, diagnostic, and preventative agents.

BACKGROUND OF THE INVENTION

The pulmonary route of administration has been used for many years for the local treatment of lung diseases; many drugs have long been valued for their local effectiveness in such treatment. In recent years, the respiratory tract has become an attractive route of administration for a large range of molecules and drug substances. Since the early 1990s, there has been an intensive growing interest in systemically delivering agents such as biotechnology derived proteins and peptides via the respiratory tract. Examples of these include anti-IgE and insulin, which are difficult to formulate orally. In addition, pulmonary inhalation is also becoming an attractive route of administration for chemotherapeutic agents, such as Doxorubicin and 5-Fluorouracil, to treat bronchogenic carcinomas.

Systemic drug absorption has recently been investigated, e.g. for the treatment of diabetes mellitus and pain treatment (Labiris N. R. & Dolovich M. B. (2003) Pulmonary Drug Delivery. Part I: Physiological factors affecting therapeutic effectiveness of aerosolized medications. Journal Clin Pharmacol. 56: 588-99). In addition, major areas of pulmonary research are currently aimed at asthma (Hardy J. G, Chadawick T. S. (2000) Sustained Release Drug Delivery to the lungs. Clin Pharmacokinet. 39:1-4), cystic fibrosis (Garcia-Contreras L, Hickey A J. (2002) Pharmaceutical and biotechnological aerosols for cystic fibrosis therapy. Advanced Drug Delivery reviews. 54: 1491-1504), lung cancer (Rao R., Markovic S. and Anderson P. (2003) Aerosol Therapy for Malignancy Involving the Lungs. Current Cancer Drug Targets. August; 3(4):239-50). and tuberculosis (Pandey R. and Khuller G. K. (2005) Antitubercular inhaled therapy: opportunities, progress and challenges. The Journal of Antimicrobial Chemotherapy. 55 (4): 430-435; Zahoor A, Sharma S, Khuller G K. (2005) Inhalable alginate nanoparticles as antitubecular drug carriers against experimental tuberculosis. International Journal of Antimicrobial Agents. 26: 298-303).

Advantages of the pulmonary route include rapid drug deposition in the target organ, using a lower dose, which results in fewer systemic side effects than other routes of administration. Another advantage of the pulmonary route is that there is no first pass metabolism.

Drug delivery to the lungs requires an aerosol vehicle, which consists of either aerosol droplets containing the drug, or powder particles of an appropriate size for lung delivery (Finlay, W. H. Mechanics of Inhaled Pharmaceutical Aerosols: An Introduction, Academic Press, 2001). The deposition of an aerosol in the lungs depends on its particle size distribution. The most common pulmonary delivery systems can be classified as nebulizers, propellant-metered dose inhaler (pMDI) and dry powder inhaler (DPI). Advances in dry powder inhalation technology and the known advantages of dry powders over solutions have made DPIs a very attractive drug delivery method. However, dry powder delivery to the lungs remains challenging due to powder aggregation which increases the particle size above the optimal particle diameter which in general terms for deep lung deposition is between 1 and 5 μm (Bosquillon C., Lombry C., Preat V. and Vanbever R. (2001) Influence of formulation excipients and physical characteristics of inhalation dry powders on their aerolization performance. Journal of Controlled Release. 70: 329-339; Dailey L. A., et al. (2003) Nebulization of biodegradable nanoparticles: impact of nebulizer technology and nanoparticle characteristics on aerosol features. Journal of Controlled Release. 86: 131-144; Lucas et al. (1999) Lucas et al. (1999) Enhancement of small particles size dry powder aerosol formulations using an ultra low-density additive. Pharmaceutical Research 16-1643-47.

As mentioned above, in order to reach the alveolar region of the lungs particles must have an adequate Mass Median Aerodynamic Diameter (MMAD) ranging from about 1 to 5 μm (Bosquillon, C. et al. (2001), supra). Larger particles are mostly deposited in the tracheo bronchial area while somewhat smaller particles are exhaled. A common technique to manufacture inhalable powders is spray drying. Here the obstacle is that powders produced by this method are more cohesive, leading to an inadequate dispersion during aerolization (Rabbani, N. R., Seville P. C., (2005) The influence of formulation components on the aerolization properties of spray dried powders. J of Controlled Release. 110: 130-140). Different strategies have been proposed in order to solve such problems. One approach is to use the advantages of large and porous aerosols particles (Edwards D. A. et al. (1998) Recent advances in pulmonary drug delivery using large, porous inhaled particles. J Appl Physiol 85: 379-85; Tsapis N, et al. (2002) Trojan particles: Large porous carrier of nanoparticles for drug delivery. Proc. Natl. Acad. Sci. 99: 12001-5). These particles possess low mass density and a larger geometric size. They are characterized by geometric sizes larger than 5 μm and mass densities around 0.1 g/cm$^3$ or less. However, such particles improve the deposition rate in the lungs but they might not influence the drug dissolution. Drug dissolution in the lungs is a prerequisite for drug uptake. Only what is dissolved can be absorbed. Davies and Feddah (2003) had shown that the dissolution rate of poorly soluble drugs is influenced by their aerosol particle size (Davies N. M and Feddah M. R. (2003) A novel method for assessing dissolution of aerosol inhaler products. International Journal of Pharmaceutics. 255:175-87).

Nanomedicine is an emerging field in biomedical sciences. Drug delivery systems involving nanoparticles have been investigated for different routes of administration. Nanoparticles are solid colloidal particles ranging from 10 to 1000 nm. They consist of macromolecular materials and can be used as adjuvants in vaccines, or as a drug carrier, in which the drug is dissolved, entrapped, encapsulated and/or to which the active principle is adsorbed or attached. Nanoparticles may act as a drug vehicle able to target tumor tissues or cells, to a certain extent, while protecting the drug from premature inactivation during the transport (Kreuter, Jorg (1991) Nanoparticle-based dmg delivery systems. Journal of Controlled Release. 16: 169-176).

The first nanoparticle-containing intravenous drug delivery system was recently approved as medicine in the United States under the name Abraxane®. It contains albumin-bound paclitaxel for the treatment of metastatic breast cancer (Abraxane [prescribing information]. Schaumburg, III: Abraxis Oncology, a Division of American Pharmaceutical Partners, Inc; January 2005). Nanoparticles have been proposed for pulmonary administration to utilize their advantages in drug delivery to the lungs (Sham J. O, Zhang Y, Finlay W. H, Roa W. H, Raimar L. (2004) Formulation and characterization of spray-dried powders containing nanoparticles for aerosol delivery to the lung. International Journal of Pharmaceutics. 269: 457-67). Furthermore, nanoparticles exhibit certain characteristics that make them ideal for pulmonary drug delivery and for treating lung specific diseases like lung cancer. Research has shown that nanoparticles avoid unwanted mucociliary clearance and in some cases phagocytic clearance (Grenha, Seijo B, Remuñán-López C. (2005) Microencapsulated chitosan nanoparticles for lung protein delivery. European Journal of Pharmaceutical Sciences. 25: 427-37) by remaining in the lung lining fluid until dissolution (Schürch S, Geiser M, Lee M M, Gehr P. (1999) Particles at the airway interfaces of the lung, Colloids and surfaces B: Biointerfaces. 15: 339-53) or translocation by the epithelium cells (Oberdörster et al. 2005 An Emerging Discipline Evolving from Studies of Ultrafine Particles. Environmental Health Perspectives. 2005.113; 823-39). One issue with pulmonary nanoparticle delivery is that their small size limits their lung deposition. Aerosolized nanoparticles have only very limited sedimentation, inertial impaction or diffusion, which causes them to be predominantly exhaled from the lungs after inhalation (Finlay et al. (2001), supra; Tsapis et al. (2002), supra; Grenha et al. (2005) supra). However, Sham et al. have shown that nanoparticles can be incorporated into carrier particles to produce the appropriate size for pulmonary drug delivery (Sham et al. (2004), supra).

In light of the foregoing, there is a need for further improvements in inhalable particles for delivery of drugs and other agents.

SUMMARY OF THE INVENTION

The present invention provides novel inhalable particles that have an active release mechanism. These novel inhalable particles have effervescent properties, and may act as carriers for active agents.

Effervescent preparations have been utilized in oral drug delivery for more than 200 years. Since that time, a large number of preparations utilizing effervescent technology have been produced including stomach distress medications, vitamin supplements, and analgesics (Eichman J. and Robinson J., 1998 Mechanistic studies on effervescent—induced permeability enhancement. Pharmaceutical Research 15. 925-930). However, effervescent powders have not previously been used for the pulmonary route of administration.

The particles of the present invention use effervescent technology. The effervescent reaction adds an active release mechanism when the particles are administered to a subject, e.g. by the pulmonary, bronchial or nasal route of administration.

In one aspect, the invention provides an effervescent powder comprising inhalable particles comprising: (i) an inorganic or organic carbonate, and (ii) an acid, the particles exhibiting effervescence when exposed to water or humid air and having a mass median aerodynamic diameter suitable for nasal, bronchial, or pulmonary administration.

In another aspect, the invention provides a method of enhancing loosening, thinning, cleansing, and removing of mucus and extrinsic surface materials from an inner surface of the nose, mouth, airway, and/or lungs of a patient in need thereof, comprising administering to the patient an effervescent powder comprising inhalable particles comprising: (i) an inorganic or organic carbonate, and (ii) an acid, the particles exhibiting effervescence when exposed to water or humid air and having a mass median aerodynamic diameter suitable for nasal, bronchial, or pulmonary administration.

In still another aspect, the invention provides a method of enhancing permeability of mucosal and surface barriers on an inner surface of the nose, mouth, airway, and/or lungs of a patient comprising administering to the patient an effervescent powder comprising inhalable particles comprising: (i) an inorganic or organic carbonate, and (ii) an acid, the particles exhibiting effervescence when exposed to water or humid air and having a mass median aerodynamic diameter suitable for nasal, bronchial, or pulmonary administration.

In another aspect, the invention provides a method of preparing an effervescent powder suitable for nasal, bronchial, or pulmonary administration, said method comprising: (i) preparing a formulation comprising an inorganic or organic carbonate, an acid, and aqueous ammonia, wherein minimal reaction occurs between the inorganic or organic carbonate and the acid; (ii) forming the formulation of step (i) into particles having a mass median aerodynamic diameter suitable for nasal, bronchial, or pulmonary administration.

In another aspect, the carbonate is sodium carbonate, and the acid is citric acid. In another aspect, the particles may comprise one or more inert filler materials such as lactose and mannitol. In yet another aspect, the particles may comprise one or more lubricants, such as polyethylene glycol and L-leucine. In another aspect, the particles may act as carrier particles for an active agent.

BRIEF DESCRIPTION OF THE DRAWINGS

FIG. 5 *a* and *b* illustrate the particle distribution of an effervescent formulation containing lactose (4 g), sodium carbonate (2.5 g), sodium bicarbonate (2.5 g) and citric acid (4 g) when different flow rates are used with the following spray drying parameters: Pump=2 mL/min, Aspirator: 8 (out of 20); Inlet temperature 64° C.; Outlet temperature 50° C.

FIGS. 7 *a* and 7 *b* show the distribution of the effervescent powders containing 1 g of lactose, 5 g of sodium carbonate and 4 g of citric acid using different inlet and outlet temperatures with the following settings: Pump: 2 ml/min; Aspirator: 10 (out of 20); Flow rate: 800 N/hl.

FIG. 12 illustrates the results of cough experiments.

DETAILED DESCRIPTION

Figure 1:
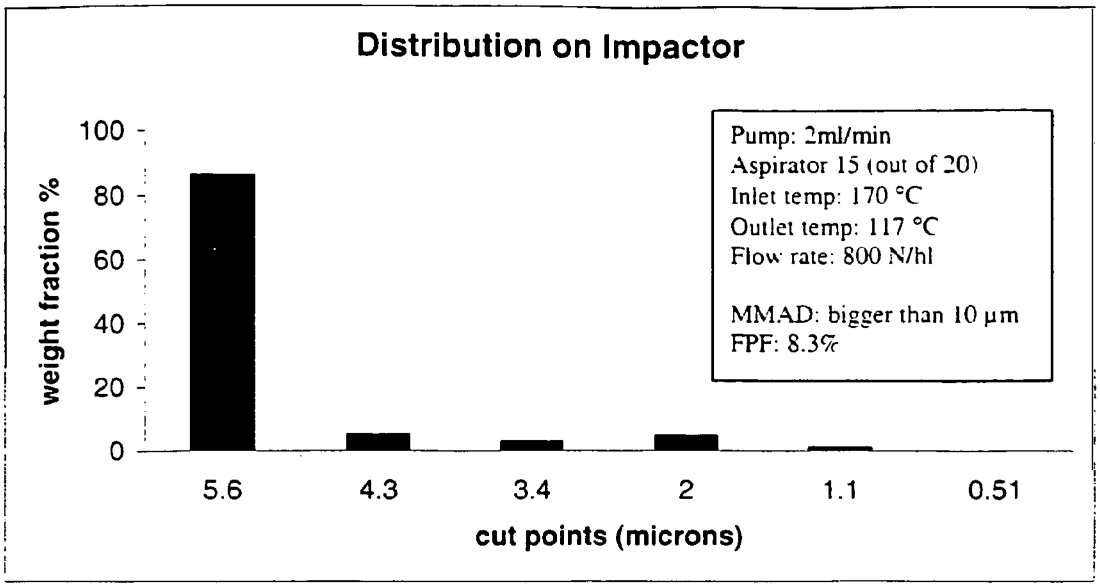
FIG. 1 illustrates the particle distribution of an effervescent formulation containing lactose (4 g), sodium carbonate (5 g) and citric acid (4 g) distributed on the plates of the Andersen Cascade Impactor when the formulation was spray dried using the following parameters: Pump: 2 ml/min; Aspirator 15 (out of 20); Inlet temp: 170° C.; Outlet temp: 117° C.; Flow rate: 800 N/hl.

In one embodiment, the invention provides an effervescent powder comprising inhalable particles comprising: (i) an inorganic or organic carbonate, and (ii) an acid, the particles exhibiting effervescence when exposed to water or humid air and having a mass median aerodynamic diameter suitable for nasal, bronchial, or pulmonary administration.

In another embodiment, the invention provides a method of enhancing loosening, thinning, cleansing, and removing of mucus and extrinsic surface materials from an inner surface of the nose, mouth, airway, and/or lungs of a patient in need thereof, comprising administering to the patient an effervescent powder comprising inhalable particles comprising: (i) an inorganic or organic carbonate, and (ii) an acid, the particles exhibiting effervescence when exposed to water or humid air and having a mass median aerodynamic diameter suitable for nasal, bronchial, or pulmonary administration.

In still another embodiment, the invention provides a method of enhancing permeability of mucosal and surface barriers on an inner surface of the nose, mouth, airway, and/or lungs of a patient comprising administering to the patient an effervescent powder comprising inhalable particles comprising: (i) an inorganic or organic carbonate, and (ii) an acid, the particles exhibiting effervescence when exposed to water or humid air and having a mass median aerodynamic diameter suitable for nasal, bronchial, or pulmonary administration.

In another embodiment, the invention provides a method of preparing an effervescent powder suitable for nasal, bronchial, or pulmonary administration, said method comprising: (i) preparing a formulation comprising an inorganic or organic carbonate, an acid, and aqueous ammonia, wherein minimal reaction occurs between the inorganic or organic carbonate and the acid; (ii) forming the formulation of step (i) into particles having a mass median aerodynamic diameter suitable for nasal, bronchial, or pulmonary administration.

In another embodiment, the carbonate is sodium carbonate, and the acid is citric acid. In another embodiment, the particles may comprise one or more inert filler materials such as lactose and mannitol. In yet another embodiment, the particles may comprise one or more lubricants, such as polyethylene glycol and L-leucine. In another embodiment, the particles may act as carrier particles for an active agent.

The term "carrier particles" as used herein is meant to include effervescent particles which contain an active agent and act as a carrier for the active agent, as well as effervescent particles which do not contain an active agent. The carrier particles may be inhaled via the nose or mouth.

The term "patient" as used herein in one embodiment refers to a mammal, and this mammal may be an animal or a human.

As mentioned above, the invention uses effervescent technology, which is normally used in tablets for oral administration, and applies this approach to the pulmonary and nasal routes. The effervescent formulation comprises an acid and a carbonate. In oral tablet formulations, effervescent formulations use a mixture of acids such as citric acid and carbonates. A typical ratio that generally achieves fast effervescent reaction and acceptable stability uses a mixture of 50% of sodium carbonate and 50% of sodium bicarbonate.

The effervescent reaction is pH-dependent. The two components react in an aqueous environment as shown in formula below, and this very simple reaction causes the production of gas which is responsible for the effervescent effect:

$$Acid+(bi)carbonate \dashrightarrow Acid\ Salt+CO_2+H_2O$$

As shown, this reaction releases carbon dioxide. The phase transition from a solid to a gas phase increases the volume and this is used in tablets to increase tablet disintegration and drug dissolution (El-Shaboury, M. H., Abd El-Gawad, A. H., Gabr, K. E., Hashem, F. M.; Effect of effervescent salt on the dissolution and bioavailability of drugs from capsules filled on a dosator-type capsule-filling machine; Pharmazeutische Industrie, Volume 55, Issue 2, 1993, Pages 176-179).

To produce inhalable effervescent powders, the first step was to establish an effervescent formulation. The basic formulation contained sodium carbonate, citric acid and water. However in order to prevent an effervescent reaction from happening before spray drying, the pH of the solution was increased using ammonia. In one aspect, an acceptable pH range is from about 5 to 14. In another aspect, the pH was maintained between 7.0 and 9.0. At this pH, the acid and carbonate react very slowly with one another. The ammonia evaporates in the spray drying process and the resulting powders contain acid and carbonate in the solid state. The resulting powder exhibits effervescent properties when it comes in contact with water, which includes contact with moisture in the air. The powder is stable under dry conditions.

The in situ formation of gas forces the carrier particles to burst and release carbon dioxide gas. The formation of small bubbles distributes drugs or nano-materials which can be incorporated into the carrier particles throughout the gas bubbles.

The effervescent reaction can be used to create airborne nano- or micro-droplets containing molecules or active principles in nano- or micro-meter scale. The effervescent reaction can also be used to interact with the mucus layers of the respiratory tract, which is discussed further in Example 1 below.

The particles may be made using an inorganic/organic carbonate and an acid material only or they may contain additional inert matrix/filler materials, e.g. lactose, mannitol, lubricants, and/or active materials such as drugs or drug delivery systems, nutrients, vitamins or diagnostics. The release of such ingredients is active over an extended surface area of the gas bubble due to the effervescent reaction.

Lactose is the most common type of excipient used for dry powder lung delivery and it is well documented in the literature (Elversson J. et al. (2003) Droplet and particle size relationship and shell thickness of inhalable lactose particles during spray drying. J. of Pharmaceutical Sciences. 92: 900-910; Karhu M. et al. (2000) Pulmonary deposition of lactose carrier used in inhalation powders. International J. of Pharmaceutics. 196: 95-103).

Suitable acids for use in the carrier particles of the present invention include any acids which are commonly used in effervescent tablets for oral administration or which have been proven to be safe for human use. Among these are citric acid, glycine citrate, fumaric acid, adipic acid, malic acid, lactic acid, ascorbic acid and tartaric acid.

Suitable carbonates for use in the carrier particles of the present invention include any carbonates which are commonly used in effervescent tablets for oral administration or which have been proven to be safe for human use. Among these are L-lysine carbonate, sodium glycine carbonate, sodium carbonate, magnesium carbonate, calcium carbonate, potassium carbonate, sodium hydrogen carbonate (sodium bicarbonate), or other salts of carbonates.

Suitable lubricants for optional use in the carrier particles of the present invention include those which have been proven to be safe for human use, particularly any such excipients considered suitable for inhalation, such as those disclosed in Bosquillon C. et al. (2001), supra; Tsapis et al. (2002), supra; and, Vanbever R. et al. (1999) Formulation and Physical Characterization of Large Porous Particles for Inhalation. Pharmaceutical Research. 16: 1735-42; the details of which are herein incorporated by reference in this regard. Examples of suitable lubricants include L-leucine and polyethylene glycol (PEG) 6000. Furthermore, surfactants also can be used to improve lung delivery; examples of which are Sodium Lauryl Sulfate, Tween 80, Polysorbate 85 (Tween 85), and Polyethylenepolypropylene glycol polymer (Pluronic F68). Suitable surfactants for optional use in the carrier particles of the present invention include those which have been proven to be safe for human use, particularly any such excipients considered suitable for inhalation (Bosquillon et al., (2001) Influence of formulation excipients and physical characteristics of inhalation dry powders on their aerosolization performance. J of Controlled Release (70) 3: 329-339).

The effervescent powders of the present invention are expected to be applicable to delivery of a wide variety of active agents. The particle size of the carrier powder governs the ultimate deposition in the lung, which can be controlled by spray-freeze drying and spray drying parameters. The final pH characteristic of effervescent powder by itself is within in vivo physiologic pH range. Appropriate conditions may be selected for preparing the carrier particles such that the biological activity of the active agents can be maintained. For instance, if active agents are known to decompose at higher temperatures, lower temperatures may be used to prepare the particles by spray freeze drying. A number of active agents have been administered via the pulmonary route using other delivery systems as noted above, further examples of which include the following: Bosquillon, C., Preat, V., and Vanbever, R. (2004) Pulmonary delivery of growth hormone using dry powders and visulization of its local fate in rats. Journal of Controlled Release 96:233-244; Codrons, V., Vanderbist F., Verbeeck R., Arras M., Lison D., Preat V., Vanbever R. (2003) Systemic delivery of parathyroid hormone (1-34) using inhalation dry powder in rats. Journal of Pharmaceutical Sciences 92:938-950; Suarez, S., O'Hara P., Kazantseva, M., Newcomer, C. E., Hopfer, R., McMurray, D. N., and Hickey, A. J. (2001) Airways delivery of rifampicin microparticles for the treatment of tuberculosis. Journal of Antimicrobial Chemeotherapy 48: 431-434.

Active agents for incorporation into the carrier particles of the present invention include active materials useful for diagnostic, preventative, or therapeutic purposes. These may include drugs, amino acids, proteins, peptides, polypeptides, diagnostics, imaging agents, enzymes, radiopharmaceuticals, nucleotides, nutrition, vitamins, hormones, immunomodulating agents, cytokines, antibodies, anti-bacterial agents, antiviral agents, mucolytic agents, bioadhesive agents, vaccines, surfactants, viscosity inducing agents, viscosity reducing agents, metal and metallic compounds, natural and herbal ingredients, chelating, binding or absorbing agents and triboluminescent materials.

Active agents also include drug delivery systems or other complex materials or bioactive structures which may be incorporated into the carrier particles. Examples of such drug delivery systems or other complex materials include drug carriers, nanoparticles, liposomes, microparticles, nanostructures, nanofibres, viruses, and bacteria.

The powder particles can be made with different Mass Median Aerodynamic Diameter (MMAD) to deliver them to different areas of interest within the respiratory tract including the bronchial region and nasal cavity. Particles suitable for delivery to the bronchial region and nasal cavity are generally larger than 5 μm (Finlay, W. H. Mechanics of Inhaled Pharmaceutical Aerosols: An Introduction, Academic Press, 2001).

Spray dryer parameters are very important to produce carrier particles with an appropriate MMAD. For example, the air flow rate of the nozzle is one of the most important parameters to influence the particle size. Higher flow rates generate smaller particle sizes due to the smaller droplet sized generated by the nozzle. The temperature determines the rate of solvent evaporation and dryness of the final powder. Furthermore, formulation composition and added excipients impact the final product. To be able to obtain inhalable particles such process and formulation parameters have to be adjusted.

EXAMPLES

Chemicals

Butylcyanoacrylate was a gift from Loctite Ltd (Dublin, Ireland). Dextran 70 (~70 kDa), L-Leucine, ammonium hydroxide and citric acid, Locust bean gum (LBG), Sodium Tetraborate Solution (STB), Rhodamine 6G and fluorescein isothiocyanate-dextran (FITC-Dextran) were obtained from Sigma Chemical Co (St. Louis, Mo., USA). Lactose monohydrate was obtained from Wyndale (Kapuni, New Zealand) or as FlowLac from Meggle, Germany. Sodium carbonate anhydrous was obtained from BDH Inc. (Toronto, ON, Canada). Sodium bicarbonate was purchased from Calcdon (Georgetown, ON, Canada). Polyethylene glycol (PEG) 6000 was obtained from Fluka Chemika-Biochemika (Buchs, Switzerland). T-MAZ 80 Polysorbate 80 was obtained from BASF (Ludwigshafen, Germany). 316 Silicone Release Spray was purchased from Dow Corning (Midland, Mich., USA). Ciprofloxacin hydrochloride hydrate was obtained from US Biological (Swampscott, Mass., USA). Doxorubicin hydrochloride for injection was obtained from USP, Mayne Pharma Inc., QC, Canada. All chemicals were of analytical grade and used as received.

Preparation of Poly (Butylcyanoacrylate) Nanoparticles (PBCN):

Butylcyanoacrylate nanoparticles were prepared by a standard procedure (emulsion polymerization) (Sommerfeld P., Schroeder U., Bernhard A. S. (1998) Sterilization of unloaded polybutylcyanoacrylate nanoparticles. International Journal of Pharmaceutics. 164: 113-118). In brief, 100 μl of the monomer was slowly added by pipette under constant stirring (600 rpm) to 10 mL HCl 0.01 N solution, containing 0.0900 g Dextran 70.000 as a stabilizer and 0.01 g of fluoresceine isothiocyanate-dextran 70.000 (FITC-Dextran) as fluorescent marker. The polymerization was carried out under stirring (600 rpm) at room temperature for 4 h. The pH of the resulting colloidal suspension was then adjusted to pH 5 to 7 using 1 N NaOH. Nanoparticles were protected from light through the polymerization process. The nanoparticles were purified from unbound dye by centrifugation at 20,000×g (Beckman Model J2-21) for 10 to 30 minutes. The particles were purified (washed) by three cycles of centrifugation and redispersion in fresh water. After centrifugation the supernatant was removed and the nanoparticles were resuspended in 1 mL of sterilized water. The fluorescent-labeled nanoparticles were stored at 8° C. and protected from the light.

Nanoparticle Size Analysis

The particle size was measured before and after spray drying using photon correlation spectroscopy (Zetasizer model HSA3000, Malvern Instruments, UK). 3 ml of fresh filtered (0.45 μm) water was filled into a disposable cuvette. An aliquot of approximately 100 μl nanoparticle suspension was added to the cuvette. Samples were sonicated for one minute immediately prior to measurement. To measure the size of nanoparticles after spray drying an adequate amount (10-100 mg) of both lactose and effervescent powder containing nanoparticles (described below) were dissolved in distilled and filtered water and sonicated immediately prior to measurements to avoid gas bubbles interfering with the measurement.

Example 1

Optimization of Formulation and Spray-Drying Conditions of Inhalable Carrier Particles (Preliminary Studies), Incorporation of Nanoparticles into Carrier Particles, and Cough Machine Experiments with Inhalable Carrier Particles Spray Drying:

The start point of this investigation was to find suitable process parameters for a basic formulation to obtain inhalable carrier particles. The effervescent particles of the present invention were formed using spray drying techniques. All formulations were spray dried using a Büchi 190 Mini-Spray Dryer (Büchi AG, Flawil, Switzerland). The nozzle orifice had a diameter 0.7 mm. Different parameters such as temperature, aspirator, and air flow were changed and are discussed below with reference to FIGS. 1 to 9. Immediately after their collection, the powders were stored in vials and kept in a desiccator.

Formulation:

To establish a base formulation of the carrier particles, the following components were used: lactose (1-10 g), sodium carbonate (2.5-5 g), citric acid (4 g), ammonia (20-30 ml 28-30% solution) and water (280-320 ml). The ingredients were weighed and added to the aqueous ammonia solution.

Variations on the base formulation are discussed in the description below, with reference to specific experiments, including those relating to FIGS. 1 to 9.

Incorporation of the Nanoparticles into the Effervescent Carrier Particles:

The nanoparticle solutions were incorporated into the carrier particles at temperatures between 150-160° C. The carrier particles were fluorescent labeled using Rhodamine G6 in order to demonstrate the active release mechanism. The carrier particles were measured using a Zeiss LSM 510 confocal laser-scanning microscope.

Confocal Laser Scanning Microscopy (CLSM):

The geometric diameter of the spray dried powders, the distribution of the nanoparticles through to the carrier particles and effervescent effect of the carrier particles were investigated using a Zeiss LSM 510 confocal laser-scanning microscope. (Oberkochen, Germany). The LSM 510 Software, version 2.01 was used to control the microscope and to analyze the images. The carrier particles examined were made by formulations and conditions as described with reference to FIGS. 9 *b-d*, except with the addition of nanoparticles to the formulation. The carrier particles were labeled with a red fluorescent label by adding 0.6 mg of methanol solution of Rhodamine G6 to 100 mL of effervescent solution to stain the carrier matrix and the nanoparticles with a green fluorescent label as noted in the procedure for preparing the nanoparticles described above. Small amounts of the powders were dispersed in immersion oil on glass slides and visually observed. The samples were observed before and after being exposed to humidity. The effervescent imaging, prior to contact with humidity, was performed using a very small amount of carrier particles containing nanoparticles dispersed in immersion oil. The oil phase prevented any contact of humidity with the particles during the observation of the images. The particle morphology (porous vs. solid) was investigated by imaging different layers of the carrier particles.

In Vitro Aerosol Deposition:

The pulmonary deposition of the empty effervescent carrier particles and the carrier particles containing nanoparticles were investigated in vitro by measuring the Mass Median Aerodynamic Diameter (MMAD) using a Mark II Andersen Cascade Impactor (Thermo Andersen, Smyrna, Ga.) in combination with a new high efficiency inhaler (described in U.S. Patent Application Publication No. 2004/0107963 to Finlay, W. H. & Wang, Z., filed Dec. 2, 2003, entitled "Device and Method for Deagglomeration of Powder for Inhalation", the contents of which are herein incorporated by reference); Wang, Z., Grgic, B., and Finlay, W. H. (2006) A Dry Powder Inhaler with Reduced Mouth-throat Deposition. J. Aerosol Med. 19(2): 168-74).

This inhaler deagglomerates powders to a higher percentage compared to conventional inhalers. It utilizes a cyclone action and mechanical impaction to disperse powder particles (U.S. Patent Application Publication No. 2004/0107963 to Finlay, W. H. & Wang, Z., supra; Wang, Z., Grgic, B., and Finlay, W. H. (2006), supra). The flow rate used was 60 l/min. This flow rate was higher than the standard flow rate of 28.3 L/min (1 SCFM) normally used in the Anderson impactor, but was more representative of human inspiratory flow rates in typical dry powder inhalers (DPIs). The Anderson impactor was recalibrated at 60 L/min, using different cut points. The following cut points were applied to perform the MMAD calculations: plate 0-5.6 μm, plate 1-4.3 μm, plate 2-3.4 μm, plate 3-2.0 μm, plate 4-1.1 μm, plate 5-0.51 μm (Voss A. and Finlay W. H. (2002) Degglomeration of dry powder pharmaceutical aerosols. International Journal of Pharmaceutics. 248: 39-50). The powder samples were weighed using an analytical balance. Also, each impactor-plate and the inhaler were weighed before and after dispersion of the powder.

Mass Median Aerodynamic Diameter (MMAD):

The MMAD was calculated by linear interpolation of the cumulative mass distribution to obtain the particle size for which the cumulative mass under this size was 50% (Sham, J.-H., Zhang, Y., Finlay, W. H., Roa, W. H. & Lobenberg, R. (2004) Formulation and characterization of spray-dried powders containing nanoparticles for aerosol delivery to the lung. International Journal of Pharmaceutics. 269: 457-467).

Fine Particle Fraction (FPF) and Geometrical Standard Deviation (GSD):

Fine Particle Fraction is defined as the particle fraction that can be delivered to the lungs. In this study the FPF was defined as the fraction of loaded powder that is collected on plates 1-6 (i.e. aerodynamic diameter<=5.6 μm, at a flow rate of 60 l/min). The Mark II Andersen Cascade Impactor was used to determine the fine particle fraction. Geometric standard deviation is a measure of the variability of the particle diameter within the aerosol (Labiris N. R. & Dolovich M. B., (2003), supra; Finlay, W. H. (2001), supra). It is defined by the ratio of the diameters of particles from aerosols corresponding to 84% and 50% on the cumulative distribution curve of the weights of particles. To calculate the GSD, a nonlinear least squares of a log-normal function was used.

MMAD Optimization:

In order to improve characteristics and MMAD of the carrier particles, different spray drying conditions were investigated, and different ingredients were added to the base formulation, such as surfactants (Polysorbate 80 and Sodium Lauryl Sulfate), ethanol, and lubricants (L-leucine and Polyethylene Glycol 6000). The influence of the total solid content in the solution was investigated by varying the lactose content between 1-10%. Other variations on the formulation were as follows:

1) 10 to 30% of ethanol was added to the solution and spray dried. This concentration can be increased up to 80%. Other organic solvents can also be used, e.g. methanol, propanolol, isopropanolol or acetone.
2) Different concentrations of surfactants (0.04% to 0.4%) such as polysorbate 80 and Sodium Lauryl Sulfate
3) 0.125 g of an amino acid L-leucine
4) 0.125 g Polyethylene Glycol 6000
5) Both L-leucine (amino acid) and Polyethylene Glycol 6000 (in above amounts)
6) Different concentration of lactose FIGS. 1-9 show the initial development of inhalable effervescent particles for deep lung deposition.

FIG. 1 shows that effervescent formulations containing spray dried lactose alone result mostly in particles larger than the required 5 μm for deep lung deposition. However, such particles may have an appropriate size to be delivered to the upper respiratory tract or the nose.

Figure 2:
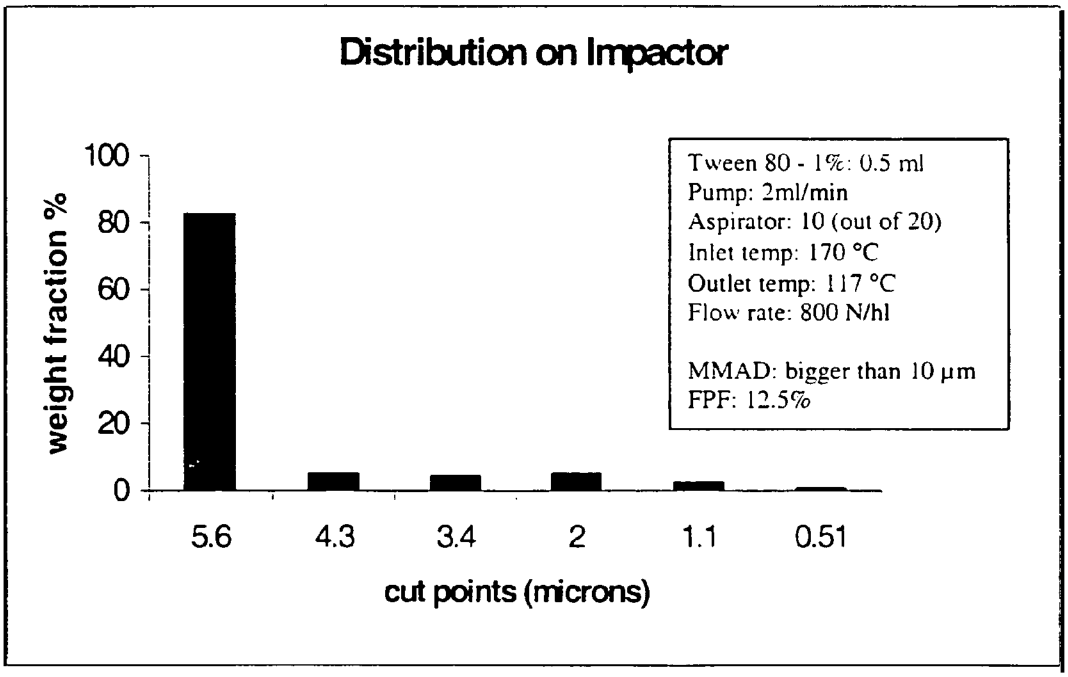
FIG. 2 illustrates the particle distribution of an effervescent formulation containing lactose (4 g), sodium carbonate (5 g), citric acid (4 g) and Tween 80 (1%-0.5 mL) distributed on the plates of the Andersen Cascade Impactor when the formulation was spray dried using the following parameters: Pump: 2 ml/min; Aspirator: 10 (out of 20); Inlet temp: 170° C.; Outlet temp: 117° C.; Flow rate: 800 N/hl
Figure 3:
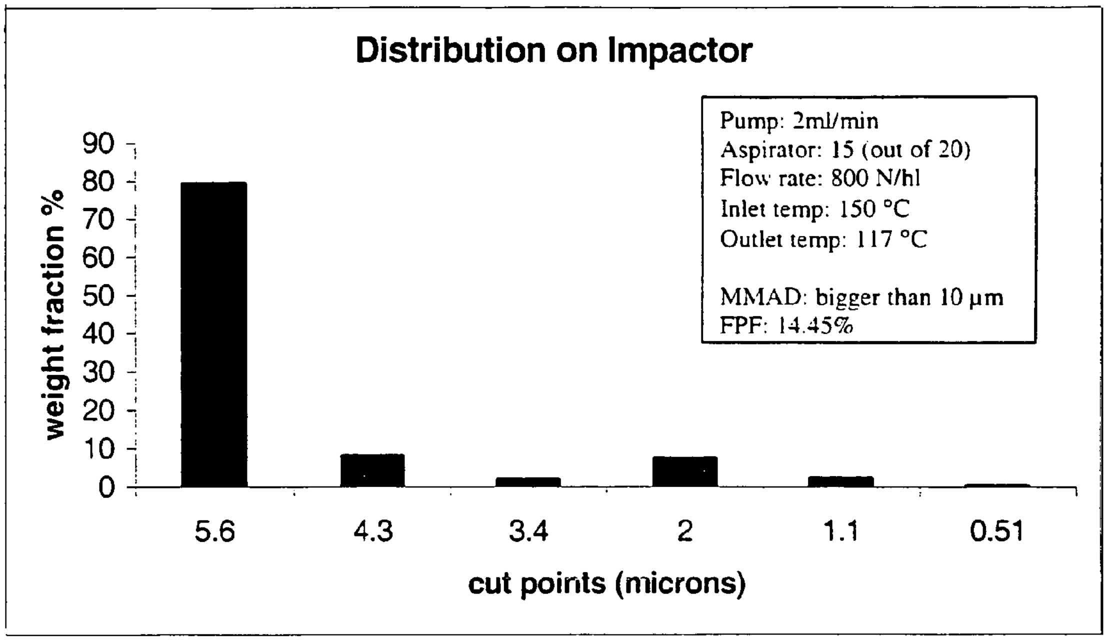
FIG. 3 illustrates the particle distribution of an effervescent formulation containing lactose (4 g), sodium carbonate (5 g) and citric acid (4 g) distributed on the plates of the Andersen Cascade Impactor. The formulation was spray dried using the same parameters as in FIG. 1 with the exception that a lower inlet temperature of 150° C. was used here.

FIG. 2 shows that the addition of different amounts of surfactants like Tween 80 does not significantly improve the particle size distribution. The fine particle fraction (FPF; defined as the particles which are able to reach the alveolar region) is still small compared to the larger particles. Similar results were observed if the inlet temperature of the spray dryer was changed. FIG. 3 shows that the FPF is still small compared to the larger particles.

Figure 4A:
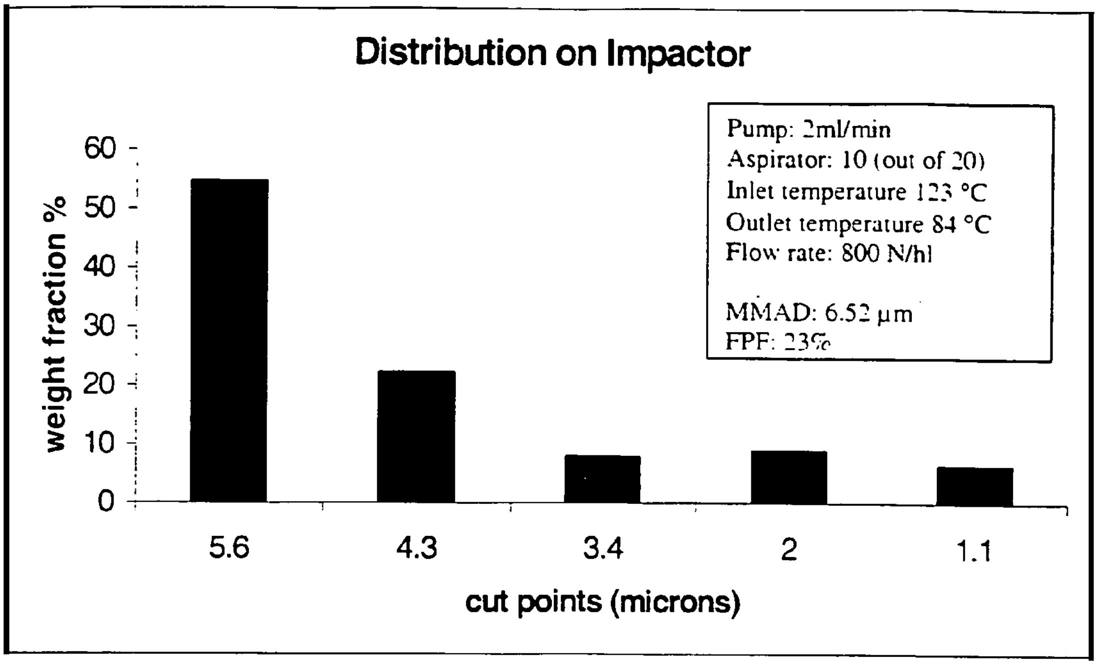
FIGS. 4 *a* and *b* illustrate the particle distribution of an effervescent formulation containing lactose (4 g), sodium carbonate (5 g) and citric acid (4 g) distributed on the plates of the Andersen Cascade Impactor when the formulation was spray dried using the following parameters: Pump: 2 ml/min; Aspirator: 10 (out of 20); Inlet temperature 123° C.; Outlet temperature 84° C.; Flow rate: 800 N/hl. Powders were collected from the collector of the spray drier (4 *a*) or from the cyclone (4 *b*).
Figure 4B:
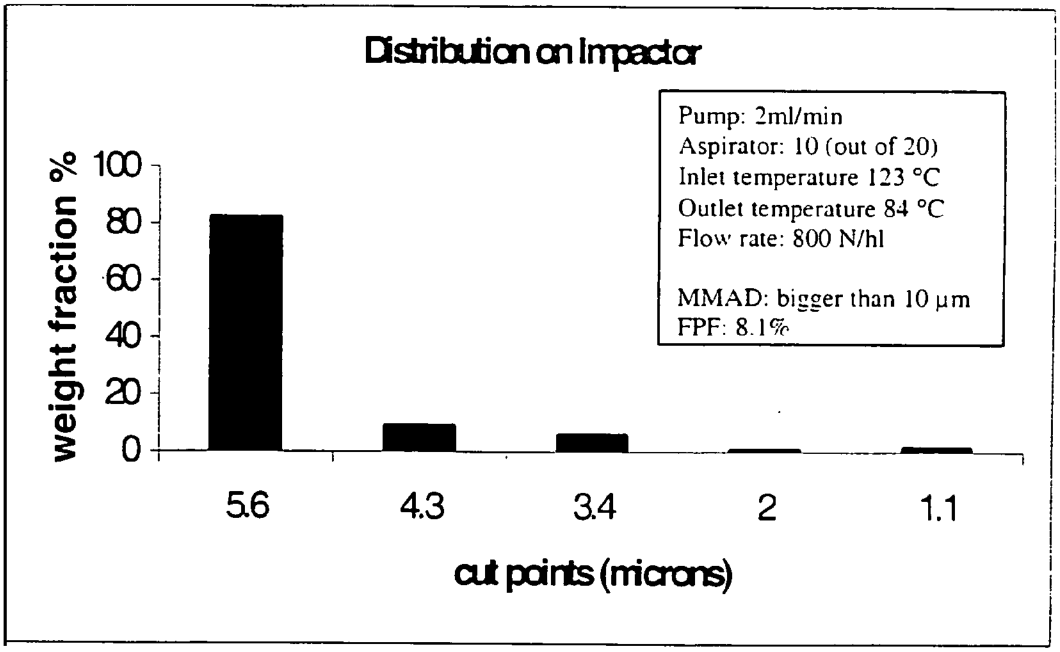

The powders in FIG. 4 were collected from the collector of the spray dryer (4 *a*) or from the cyclone (4 *b*). The results show that larger particles adhere to the wall of the spray dryer easier compared to the smaller particles. The MMADs for both experiments were bigger than 10 μm.

Figure 5A:
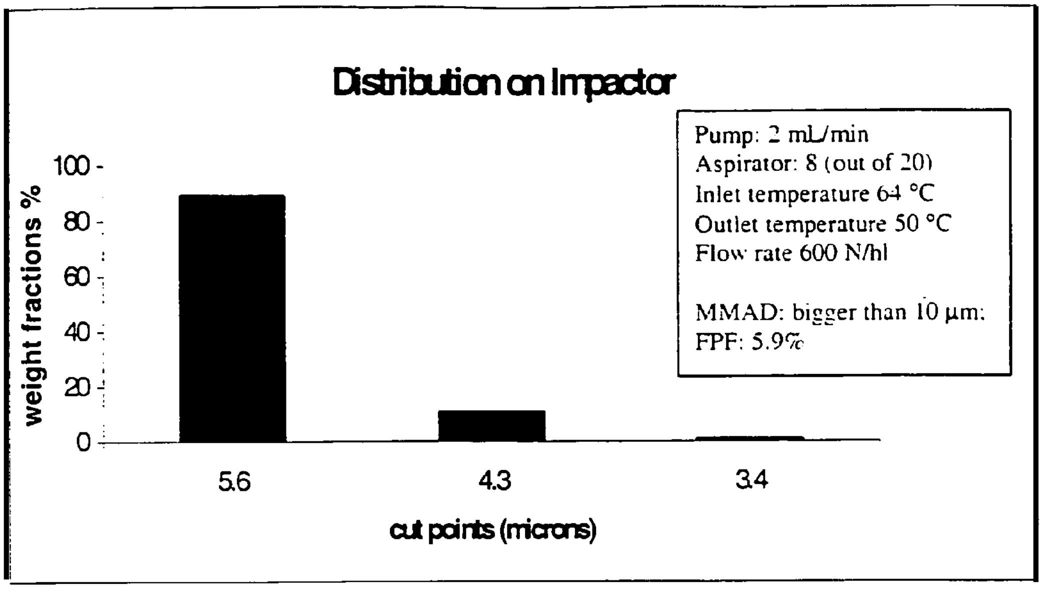
FIG. 5*a* shows the distribution of the powders on the Andersen Cascade impactor when a flow rate of 600N/hl was applied.
Figure 5B:
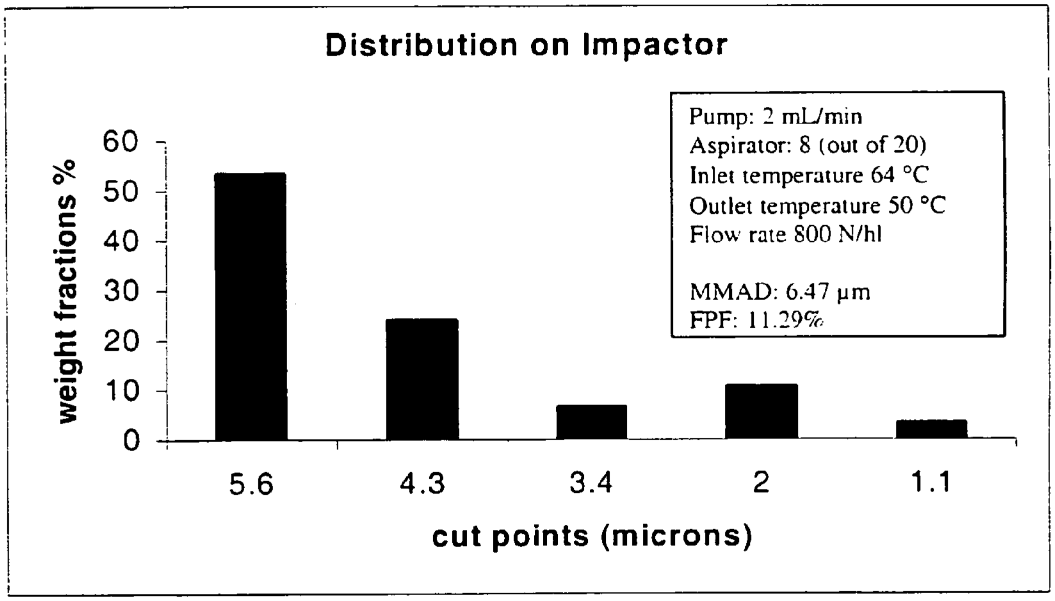
FIG. 5*b* shows the distribution of the powders when a flow rate of 800 N/hl was used.

The experiments shown in FIGS. 5 A/B illustrate the influence of the air flow rate used in the spaying nozzle. If the flow rate is high more smaller particles result as compared to lower flow rates. The best results were obtained when a flow rate of 800 N/hl was used. The MMAD was 6.47 μm for a flow rate of 800 N/1 h and when a flow rate of 600 N/1 h was applied a MMAD of 10 μm was achieved.

The experimental conditions were chosen in this experiment to further show that it is possible to use bicarbonate as an excipient. Sodium bicarbonate decomposes at temperatures above 50° C. Mixtures of carbonate and bicarbonate or bicarbonate can be used as excipients if lower temperatures are used to synthesize such carrier particles. It was investigated if lower spray drying temperatures can be used to make carrier particles. As shown in FIGS. 5 *a* and *b*, the conditions used resulted in carrier particles which were not suitable for deep pulmonary administration (most of the particles having a MMAD larger than 5 μm).

Figure 6:
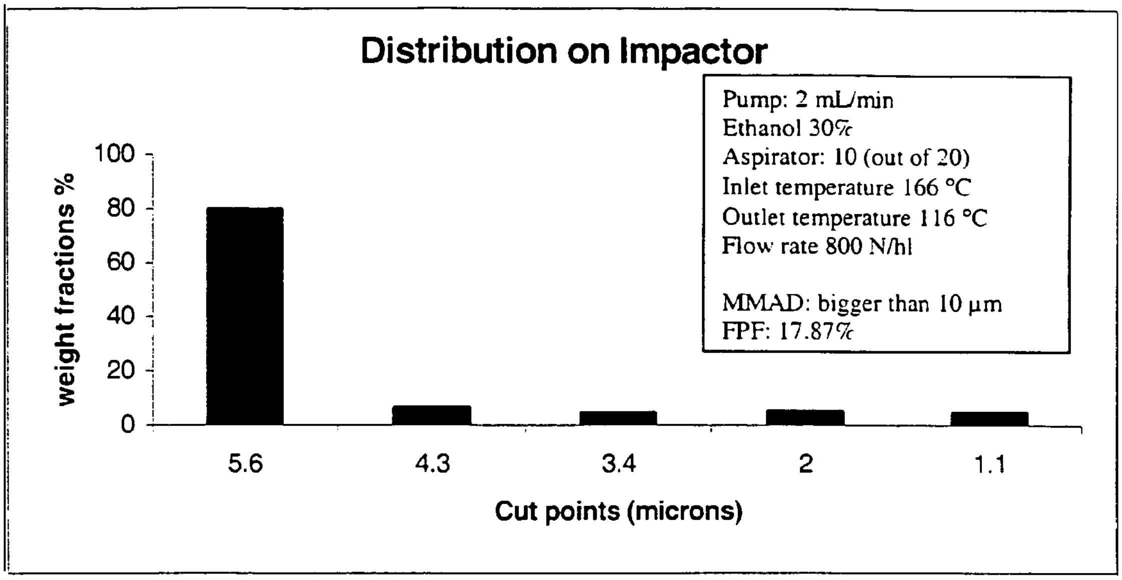
FIG. 6 illustrates the particle distribution of the effervescent formulation when 30% Ethanol was added to the formulation containing lactose (4 g), sodium carbonate (5 g) and citric acid (4 g). The formulation was spray dried using the following parameters: Pump: 2 mL/min, Aspirator: 10 (out of 20); Inlet temperature 166° C.; Outlet temperature 116° C.; Flow rate 800 N/hl.

The experiments in FIG. 6 show that the addition of ethanol did not result in an significant improvement in the FPF. The addition of volatile solvents like ethanol can cause a decrease in particle density while the geometric radius might be unchanged.

Figure 7A:
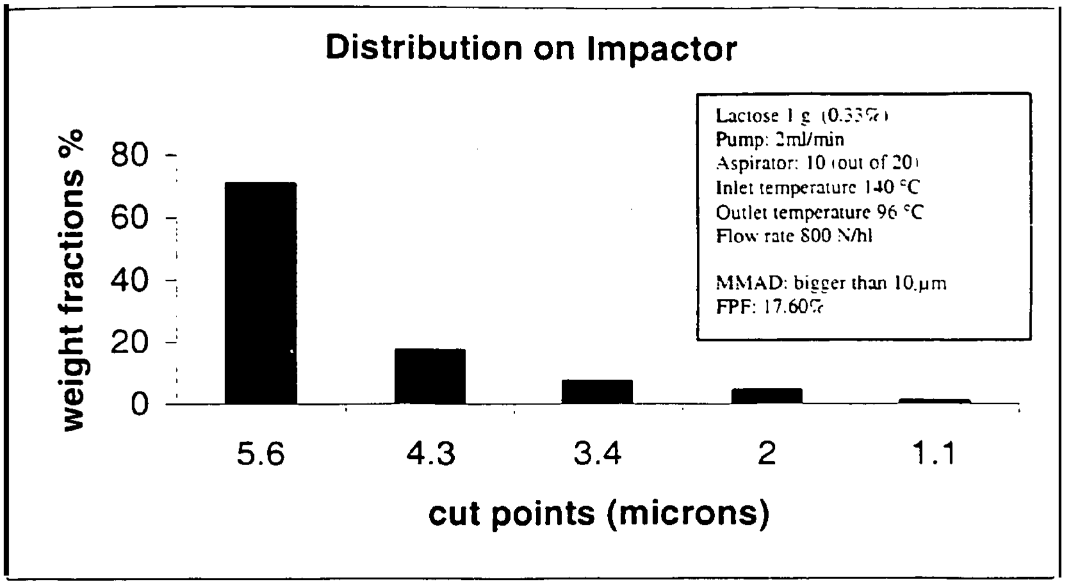
FIG. 7*a* shows the results with an inlet temperature of 140° C. and outlet temperature of 96° C.
Figure 7B:
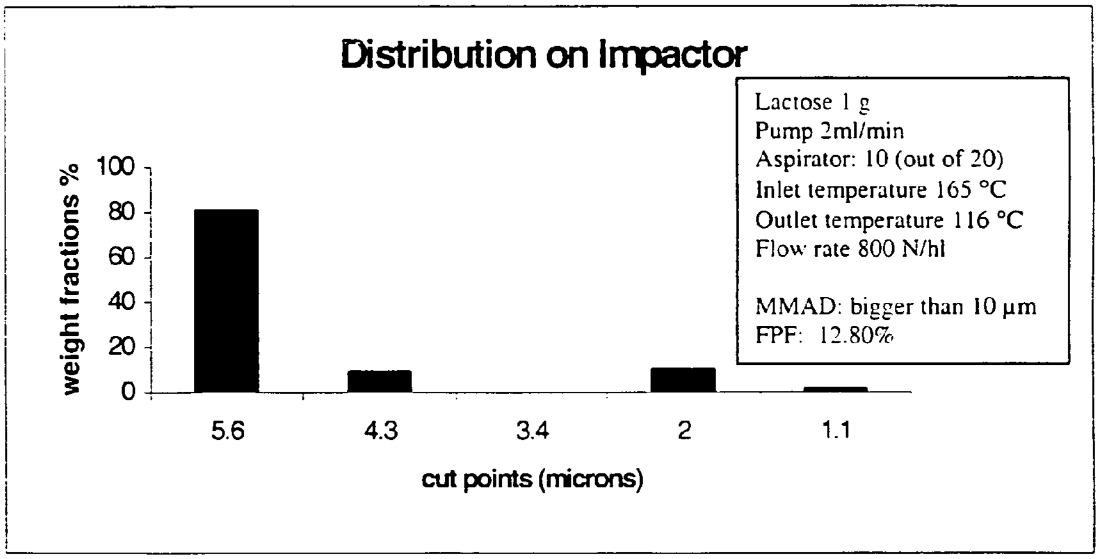
FIG. 7*b* shows the results with an inlet temperature of 165° C. and outlet temperature of 116° C.

The influence of the inlet temperature is shown in FIGS. 7 A/B. As shown, the FPF is influenced by the temperatures used for the spray drying process.

Figure 8:
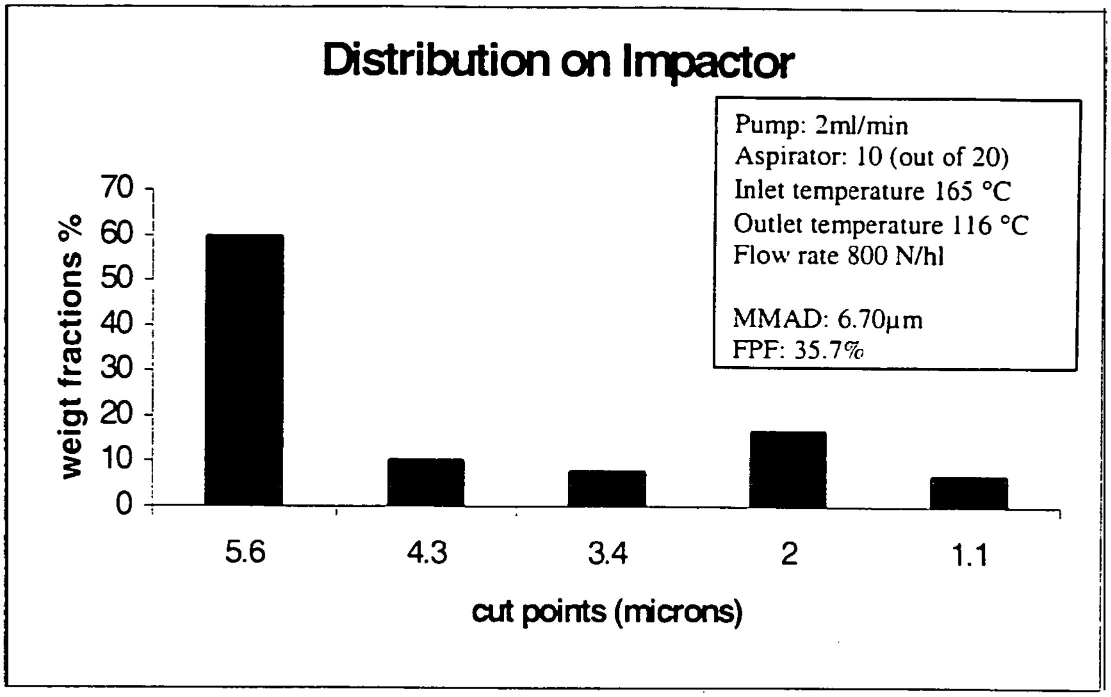
FIG. 8 illustrates the results for powders that were first spray dried and afterwards jet milled. The powder was spray dried using the following parameters: Pump: 2 ml/min; Aspirator: 10 (out of 20); Inlet temperature 165° C.; Outlet temperature 116° C.; Flow rate 800 N/hl.

FIG. 8 shows the combination of spray drying and milling. The results showed an improvement when compared with powders that were just spray dried. The FPF increased compared to powders which were not milled. However, spray drying and jet milling even with an improvement in particle size it is not an option to produce such particles, since the consuming time and cost is too high.

FIG. 9 A-D shows the influence of adding lubricants to the formulation. As shown, the FPF increases when these excipients are used. In this example, the mean particle size of the FPF can be reduced if the aspirator setting is increased. Formulations with an appropriate MMAD for deposition in the alveolar region of the lung were obtained if L-leucine and Polyethylene glycol 6000 (PEG) were added to the solution (5 mL each of a 2.5% solution). The best results were obtained by using a liquid feed rate of 2 mL/min, a pump flow setting of 3 (out of 10), aspirator 15 (out of 20), an air flow of 800 N/hl and an inlet temperature between 120-133° C. The corresponding outlet temperature was kept between 80 and 92° C. The MMAD of these formulations ranged from 2.8 to 3.60 μm (FIGS. 9*b* to 9*d*; FIGS. 9*c* and 9*d* represent duplicate experiments). Such carrier particles are suitable for alveolar lung deposition. Appropriate MMADs were also obtained when the following parameters were used: a liquid feed rate of 2 ml/min, a pump flow setting of 3 (out of 10), aspirator 15 (out of 20), an air flow of 800 N/hl, and an inlet temperature between 155-165° C. The corresponding outlet temperature was kept between 100-110° C.

These experiments were repeated as shown in Example 2 below under similar conditions and similar results were obtained. Both ingredients work as a lubricant in the resulting powders (Rotthauser, B., Kraus, G., Schmidt P. C. (1998) Optimization of an effervescent tablet formulation containing spray dried L-Leucine and polyethylene glycol 6000 as lubrificants using a central composite design. European Journal of Pharmaceutics and Biopharmaceutics. 46: 85-94). The additional presence or absence of butylcyanoacrylate nanoparticle suspension in the solution had no significant influence on the MMAD of the carrier particles.

Figure 10:
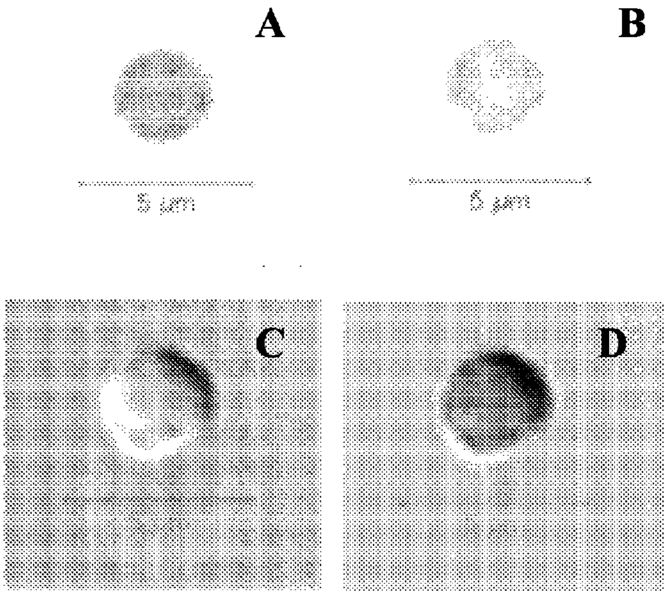
FIG. 10 shows nanoparticles which are incorporated into carrier matrix, and it can be seen that the carrier matrix is continuous. A) green channel (nanoparticles), B) red channel (carrier matrix) C) normal light, D) superimposed
Figure 11:
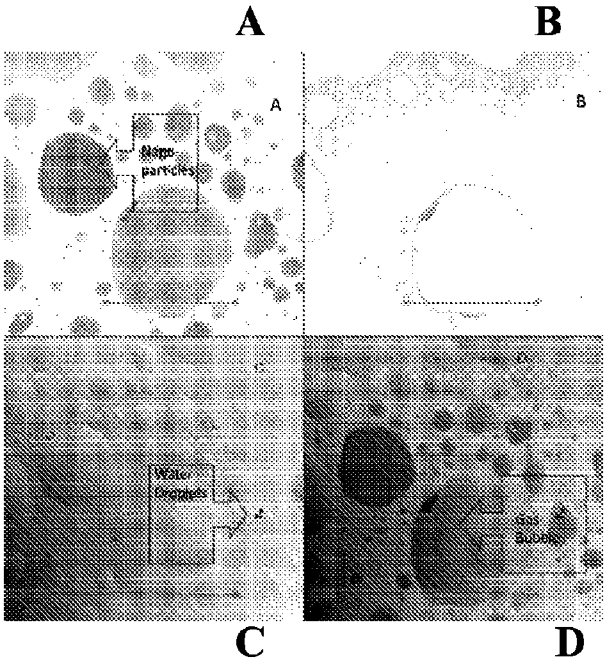
FIG. 11 shows gas bubbles after effervescent particles were exposed to humidity, illustrating that the nanoparticles are within the gas bubble while the carrier matrix dissolves: A) green channel (nanoparticles), B) red channel (carrier matrix) C) normal light, D) superimposed.

The effervescent properties of the carrier particles were visible as small air bubbles in aqueous medium. The particle size of the nanoparticles did not significantly change after spray drying. FIGS. 10 and 11 illustrate the effervescent reaction of a carrier particle prepared using the formulation and conditions as described for FIG. 9*b-d*, except that the carrier particles were loaded with polybutylcyanocarylate nanoparticles.

The pictures in FIG. 10 were taken using either normal light (picture C) or pictures were taken using a red or green channel. In the red channel, only red fluorescent light from the dye added to the particle matrix can be seen; in the green channel only green fluorescent light can bee seen. The nanoparticles were made by substituting 10% of the dextran 70 amount with FITC-labelled dextran instead. Therefore, some of the FITC-Dextran is incorporated into the nanoparticles and the nanoparticles can be visualized as green dots. This technique of staining allows to differentiate visually between different components of a formulation. FIG. 10 shows that the carrier particle is a continuous matrix. The nanoparticles are distributed throughout the carrier matrix. Both kinds of particles (hollow and continuous are normally observed in such powders).

FIG. 11 shows gas bubbles after the particles shown in FIG. 10 were exposed to humidity. The nanoparticles (green channel) are visible within the gas bubble while the carrier matrix (red channel) dissolves. FIGS. 10 and 11 demonstrate the effervescent reaction of the powders. Particles of about 5 μm diameter expand to bubbles of over 30 μm after being exposed to humidity.

By varying the lactose amounts between 1-10%, this resulted in 1.20%-33.3% total solids in the solution. The results show that different concentrations of lactose influence the size and shape of the carrier particles. Higher total solid content in the solution caused bigger particles sizes due to higher solid content in each droplet.

Polysorbate 80 and Sodium Lauryl Sulfate are surfactants used to decrease the agglomeration tendency between particles. Adding these excipients also decreased the attachment of the particles to the wall of the cyclone however it didn't show any improvement on the MMAD of the carrier particles.

In one set of experiments, only lactose (7%) was used. Again, if ethanol was added to the solution, the particles became larger and the particle densities decreased. In this case the concentration of 30% of ethanol was not enough to improve the MMAD of the carrier particles. Bigger carrier particles decrease the agglomeration tendency of the powder as described by other researchers (Elversson, J. et al. (2002) Droplet and Particle Size Relationship and Shell Thickness of Inhalable Lactose Particles during Spray Drying. Journal of Pharmaceutical Sciences. 92: 900-910). The same effect of bigger particles and lower density was observed when ammonia was used in the basic formulation. Results obtained from the different formulations above showed that each excipient had an impact on the shape, size and particle moisture content.

For a number of these formulations the mass median aerodynamic diameter was larger than 8 μm. According to literature, no deposition will occur in the alveolar region of the lung. Most of the deposition will occur in the upper respiratory tract.

This example shows that it is possible to produce carrier particles for respiratory drug delivery that incorporate effervescent technology. The effervescent reaction adds an active release mechanism when the particles are administered to a subject, e.g. by the pulmonary, bronchial or nasal route of administration.

The carrier particles may be loaded with nanoparticles, which they release actively upon contact with water. The carrier particles can be made with an appropriate MMAD to reach the alveolar region of the lung. To achieve the desired MMAD spray drying parameters as well as formulation factors have to be optimized for the effervescent formulations before a suitable MMAD for deep lung deposition can be achieved.

Cough Machine Experiments with Inhalable Carrier Particles

Methods:

Mucus simulants (MS): The MS vary from a non viscous, non-elastic substance, for example water, to a MS of different degrees of viscosity and elasticity. MS viscous-only were prepared with a 0.5% locust bean gum (LBG) in a Ringer solution. To create elasticity, different amounts of Sodium Tetraborate Solution (STB) were added to the LBG solution.

0.5% LBG: 100 ml of Ringer solution was heated to 80° C. and 0.5 mg of the LBG powder was added slowly to the hot solution while stirring to prevent it from clumping together. The solution was then cooled to room temperature. Coomassie blue was added in an amount of 0.15 mg per 100 ml and the solution was stored in 1.5 ml aliquots at 4° C.

A 0.01 M solution of Sodium Tetraborate was prepared by dissolving 3.814 g of STB in 100 ml of water.

Cough Machine Preparation:

The weight of the sample was determined by weighing the removable nozzle end-piece of the cough machine before and after the experiment on an analytical balance. The sample size was approximately 0.5 ml of 0.5% LBG. It was placed about 40 cm inside the end-piece of an artificial trachea. The artificial trachea is described in King et al, 1985. Clearance of mucus by simulated cough. J. Appl. Physiol. 58 (6) 1776-1782. The artificial cough flow was set to a pressure of 8 psi which corresponds approximately with the amount of pressure generated by a normal adult cough.

Experiments

The first set of experiments used viscous MS without elasticity—its composition was 0.5% LBG solution. The sample was placed into the cough machine. Each experiment was repeated three times for each concentration.

The second set of experiments was performed in the same way. However, here MS with viscosity and elasticity was used. Different amounts of Sodium Tetraborate (1 to 10 droplets) were added to a 0.5% LBG solution.

Figure 9A:
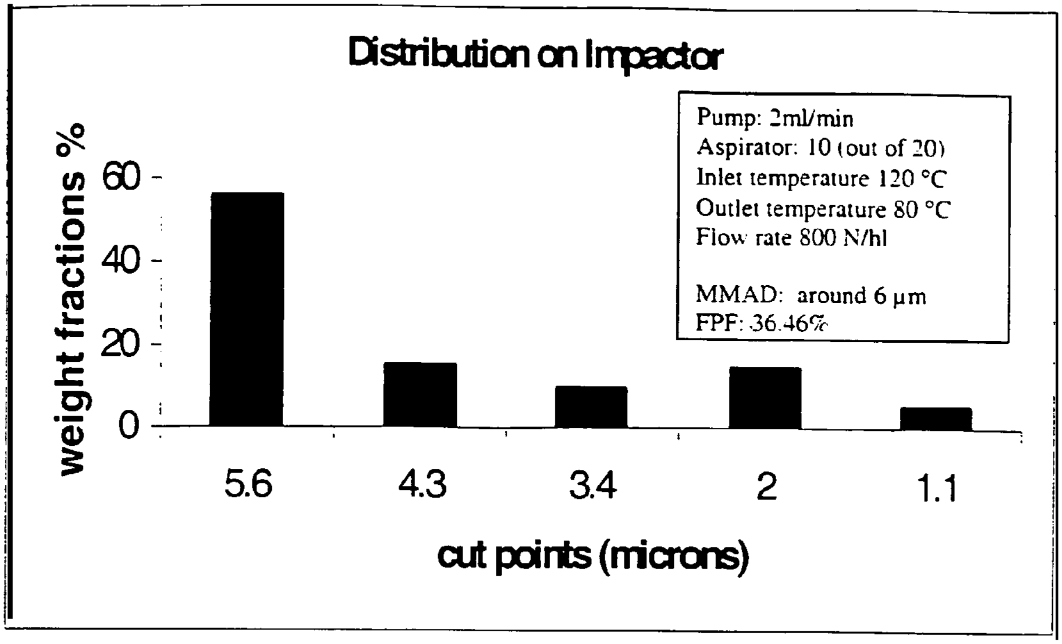
FIGS. 9 *a, b, c* and *d* illustrate the particle distribution of the effervescent formulation when lactose (4 g), sodium carbonate (5 g), citric acid (4 g), L-leucine and polyethylene glycol 6000 (5 mL each from a solution of 2.5% (w/w) in their formulations. The formulations were spray dried using the following parameters: Pump=2 mL/min; Aspirator: 10 or 15 (out of 20); Inlet temp: 120 to 133° C.; Outlet temp: 80-92° C.; Flow rate: 800 N/hl.
FIGS. 9*c* and 9*d* represent duplicate experiments.
Figure 9B:
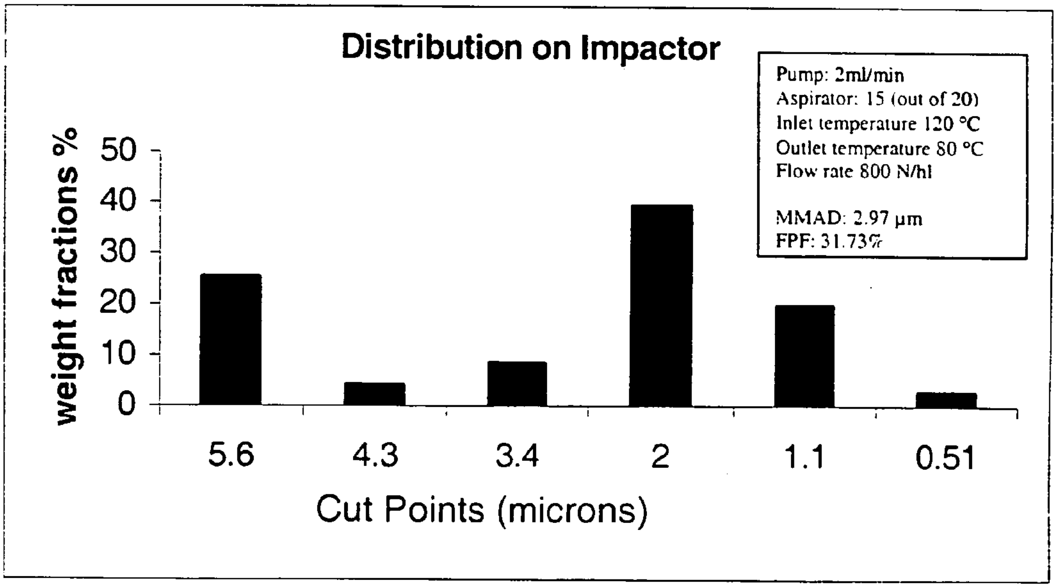
Figure 9C:
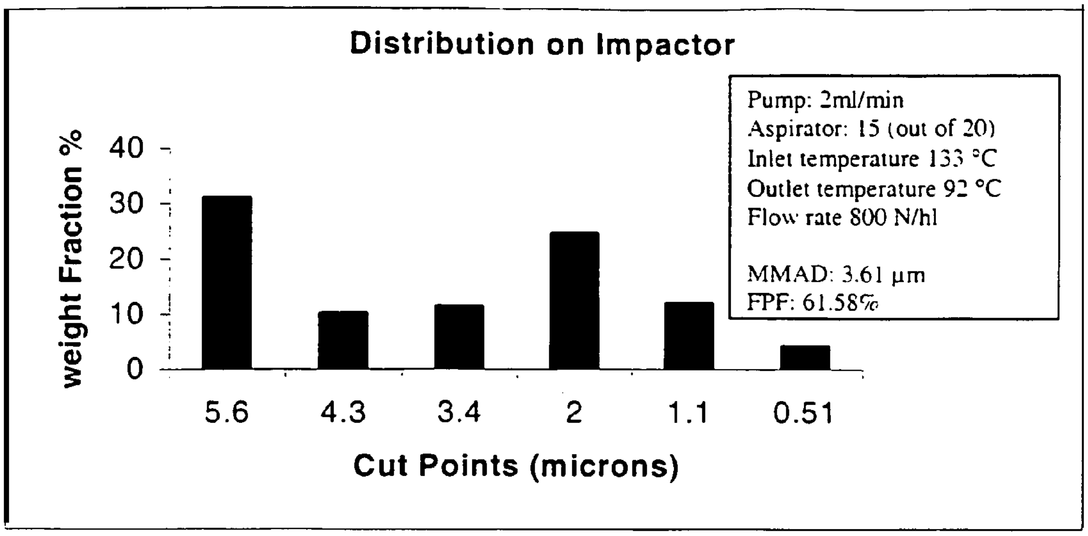
Figure 9D:
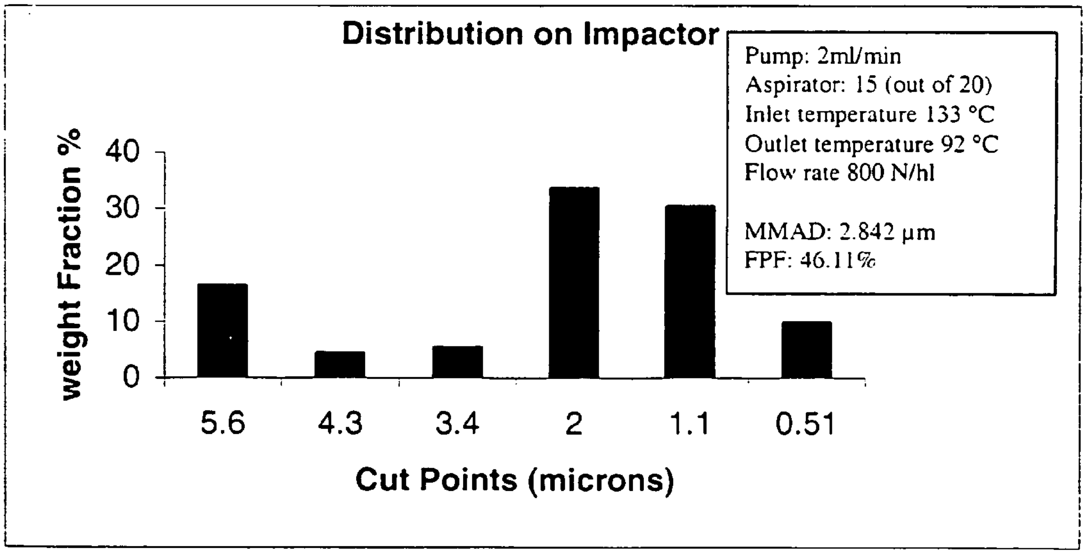

In the third set of experiments, effervescent powder formulations prepared as described for FIG. 9*b-d* were tested using viscous and elastic MS. The powders were mixed with an appropriate amount of MS, centrifuged and loaded into the machine.

Figure 12A:
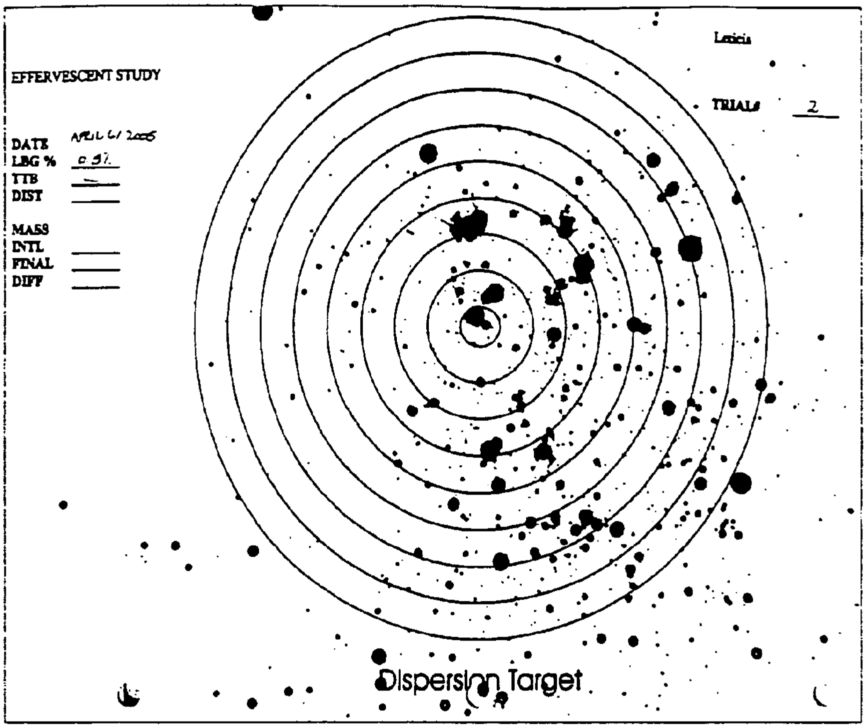
FIG. 12A illustrates representative results obtained with mucus simulant alone.
Figure 12B:
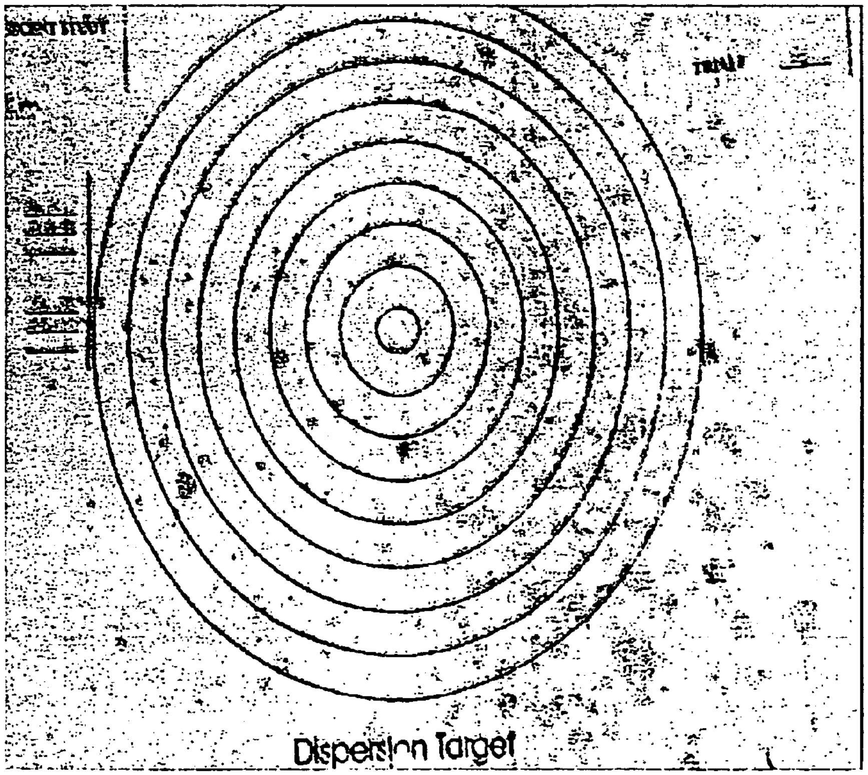
FIG. 12B illustrates results obtained when the mucus simulant contains effervescent powder.

Results:

The recorded pattern of the mucus from the cough machine clearly showed differences between control MS or MS treated with effervescent powders (FIGS. 12*a* and 12*b*). Similar results were observed if MS with different degrees of viscosity and elasticity was used. Factors like concentration of locust bean gum and addition of STB influenced the pattern. However, the control showed in most cases large deposits and some big clusters of deposits on the graphs (FIG. 12*a*). If effervescent powders were used, the MS showed more and smaller deposits (FIG. 12*b*). Fewer clusters were observed using the effervescent powders. These graphs generally showed more and smaller points. These results show that effervescent powders are able to disperse the MS and make the MS less adhesive. Such properties can be used therapeutically to loosen mucus in different sections of the respiratory tract.

Example 2

Continued Optimization of Formulation and Spray-Drying Conditions of Inhalable Carrier Particles, and Incorporation of Nanoparticles and Ciprofloxacin into Carrier Particles In this study, polybutylcyanoacrylate nanoparticles and ciprofloxacin, a poorly water soluble drug, were used as two different model substances for pulmonary delivery. Drug release and dispersion of nanoparticles were separately compared using lactose carrier particles (that dissolve without effervescent reaction) and the new effervescent carrier particles.

Preparation of Empty Carrier Particles and Ciprofloxacin Carriers:

7 g of lactose monohydrate were used to prepare the spray dried samples. Lactose was added to 100 mL of distilled water. To produce the new carrier particles, different formulations that are used in effervescent tablets were tested, as noted in Table 1 below. Sodium carbonate as a salt and citric acid were tested using different concentrations.

TABLE 1

| | Ingredients used | Concentration tested (%) |
|---|---|---|
| Carbonates | Sodium Carbonate | 0.75%-1.5% |
| Acid | Citric Acid | 1.2% |
| | Ammonia | |
| Lubricants | L-leucine | 0.8-1% |
| | Polyethylene glycol 6000 | 0.8-1% |
| Alcohols | Ethanol | 10-30% |
| Surfactants | Polysorbate 80 (Tween 80), Sodium Lauryl Sulfate | 1% |

0.6 mg of methanol solution of Rhodamine G8 was added to 100 mL of effervescent solution to stain the carrier matrix.

To prepare the effervescent formulations, solid ingredients were weighed and added to an aqueous ammonia solution. The effervescent solutions were prepared using 4 g of lactose, 4 g of citric acid, 5 g of sodium carbonate, 20 mL of ammonia (28-30% solution), 290 mL of water, and other ingredients as noted above in Table 1. The pH was maintained at approximately 8.0 to 9.0. Carrier particles containing ciprofloxacin were prepared using 100 mg of ciprofloxacin. The drug was first dissolved in 10 mL of HCl 0.01N and then added to 100 mL of a solution containing only lactose and water, and to 100 mL of the effervescent solution, which was prepared as above except that 5 μL each of a 2.5% solution of L-leucine and 2.5% solution of PEG 6000 was also added to the formulation. A Buchi 190 Mini-Spray Dryer (Buchi AG, Flawil, Switzerland) was used to produce the carrier particles. The diameter of the nozzle was 0.7 mm.

In each experiment 100 mL of either lactose solution (7 g of lactose monohydrate in 100 mL distilled water) or effervescent solution was spray dried at an inlet temperature 120° C.-160° C., an outlet temperature of 90-120° C., and an aspirator setting of 15 (out of 20), the air flow in the nozzle was 800 NormL/hr and a feed rate of 2 mL/min was used. The spray dried powders were collected in vials. Immediately after their collection, the powders were stored in a desiccator over silica gel.

Determination of Ciprofloxacin Loading Efficiency:

15 mg of the effervescent and lactose powders were dissolved in 100 ml of water. Before the measurements the samples were filtered (0.22 μm). The dissolved ciprofloxacin content was analyzed using UV spectroscopy at $\lambda$=271 nm (SPECTRONIC 3000 ARRAY—Milton Ray). A calibration curve was established, the correlation coefficient for the calculated linear regression was 0.9999 and the correlation equation was used to determine the dissolved drug content.

Incorporation of the Nanoparticles into Carrier Particles and Fluorescent Labelling:

7 mL of a suspension containing polybutylcyanoacrylate nanoparticles (prepared as noted above) were added to the lactose or the effervescent solution. The lactose solution was spray dried at temperatures between 150-160° C. and the effervescent solution was spray dried at temperatures between 120-140° C.

Physico-Chemical Characterization of the Nanoparticles and the Carrier Particles:

Particle size and FPF were determined as noted above in Example 1. The dispersibility and content of ciprofloxacin of the spray-dried powders was determined using a Mark II Andersen impactor. Following impaction, each impactor plate from the Andersen cascade impactor and the inhaler was washed with 5 ml of distilled water. The resulting solutions containing the powder from the plate were kept in centrifuge tubes. The solutions were analyzed for ciprofloxacin content using UV spectroscopy (UTV Absorbance at $\lambda$=271 nm) The dissolved drug content was determined as noted above. The MMAD was calculated by a nonlinear regression fit of a log-normal function to the data.

Scanning—Electron Microscope (SEM):

The carrier particles sizes and shapes were investigated using a Hitachi S-2500 scanning electron microscope (S2500 SEM, Hitachi, Tokyo, Japan). The lactose and effervescent powders were sprinkled onto a stub with silicon from a sticky tab. The unbound powders were dusted out by an air gun. The samples were coated with gold sputter using a S150B Sputter Coater (BOC Edwards, Crawley, West Sussex, UK) and examined using a scanning electron microscope.

Confocal Laser Scanning Microscopy (CLSM):

This was performed as described in Example 1.

Figure 13:
FIG. 13 illustrates an SEM image of typical lactose particles observed after spray drying of a 7% of lactose solution.

Results:

Different powder compositions were tested in order to produce carrier particles with an appropriate size. Blank lactose carrier particles were spray dried at inlet temperatures between 140-160° C. The MMAD of the carrier particles was analyzed using the Andersen cascade Impactor. 10 samples of lactose carrier particles were analyzed and the mean MMAD was found be 10 μm or larger. The FPF was found to be 13.86%+/−5.56 (n=8). FIG. 13 shows a lactose powder which was made without the presence of any other solvent or excipients. The image shows that the majority of the particles in this powder were spherical.

Different ingredients such as ethanol, Tween 80, L-leucine and PEG 6000 were added to the basic formulation to improve the particle size and to achieve an appropriate MMAD. In addition, different concentrations of lactose were tested.

Figure 14:
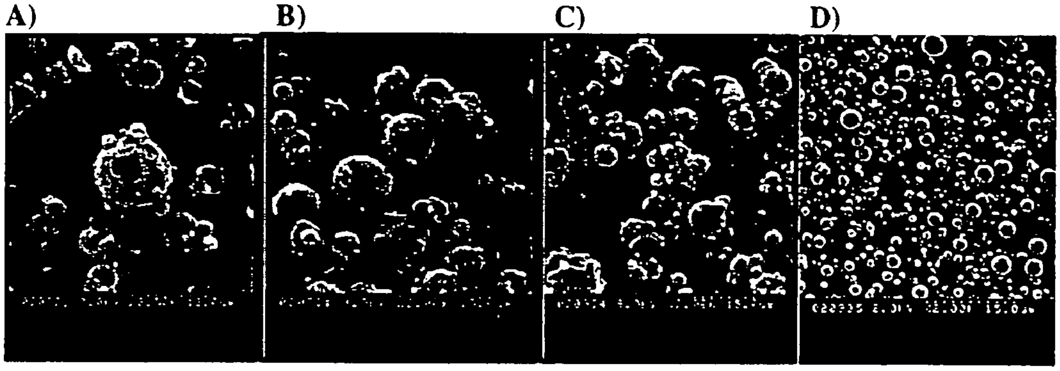
FIG. 14 shows a sequence of SEM pictures with increasing concentrations of lactose.

Different amounts of lactose had a large impact on the size and morphology of the carrier particles. Increasing the amount of lactose led to smaller and denser particles and also produced particles with more spherical shape. These results are in agreement with results reported by Vanbever et al. (1999), supra. FIG. 14 shows a sequence of SEM pictures with increasing concentrations of lactose.

Ethanol was added to the formulation with the objective of producing larger porous particles with a lower density. However our results showed that when ethanol was used it did not improve the particle size or the morphology of the carrier particles. The MMAD was still approximately 8.5 μm and not suitable for deep lung deposition. This might be due to the relatively low ethanol concentrations used, which were between 10-30% v/v. Other studies have reported using up to 70% of the total volume of ethanol to produce porous particles. (Tsapis et al. (2002), supra).

Tween 80 also did not show any improvement in particle size when compared to the lactose formulation.

A large improvement in particle size and MMAD was observed when 5 mL each of a 2.5% solution of L-leucine and 2.5% solution of PEG 6000 were added to the formulation. For these effervescent carrier particles the average MMAD was 2.17 μm+/−0.42, FPF was about 46.47%+/−15 and the GSD was 2.00+/−0.06 (see Table 2).

TABLE 2

Different formulations used for spray drying and their size distribution.

| Powder | MMAD (μm) | FPF (%) | GSD |
|---|---|---|---|
| Blank lactose (7%) | 10 | 13.86% +/− 5.56 | — |
| Ethanol 30% | 8.5 +/− 1.8 | 17.87 +/− 4 | — |
| Lactose 10% | 10 | 17.60 +/− 3.5 | — |
| Tween 80 | 10 | 12.50 +/− 2 | — |

TABLE 2-continued

Different formulations used for spray drying and their size distribution.

| Powder | MMAD (μm) | FPF (%) | GSD |
|---|---|---|---|
| L-leucine and PEG 6000 | 2.17 +/− 0.42 | 46.47% +/− 15 | 2.00 +/− 0.06 |

Figure 15:
FIG. 15 illustrates a scanning electronic micrograph of inhalable effervescent particles containing L-leucine and PEG 6000 as excipients. Some asperities are present on the surface of the carriers due to the presence of PEG 6000.

Using L-leucine and PEG 6000 in the effervescent formulation, it was possible to obtain inhalable particles as indicated by the SEM pictures in FIG. 15. These particles also show a more irregular morphology when compared to the highly spherical lactose carrier particles.

Comparisons of Drug Release from Effervescent and Conventional Carrier Particles:

Ciprofloxacin is a potent and broad-spectrum antibiotic that is poorly water soluble at physiological pH. The drug release of ciprofloxacin from conventional lactose particles was compared with the effervescent formulation. The results show that the effervescent carrier particles released 56+/−8% into solution compared with 32+/−3% when lactose particles were used, which is a significant difference (t-test, P<0.05). The remaining drug was visual as precipitate before filtering the solution. In this experiment, ciprofloxacin was used as a model drug in order to evaluate the effect of active drug release from the carrier particles compared to passive release and dissolution. It was found that the effervescent carrier particles were able to increase the drug dissolution. Rygnestad et al. (2000) reported that effervescent paracetamol tablets were absorbed significantly faster compared to conventional tablets (Rygnestad et al. (2000) Absorption of effervescent paracetamol tablets relative to ordinary paracetamol tablets in healthy volunteers. European J of Clinical Pharmacology 56: 141-143). Dosage form disintegration and drug dissolution are typically increased when effervescent formulations are used. Therefore, it is envisioned that an effervescent inhalable powder can increase the absorption and bioavailability of drugs in the lungs.

Results from the cascade impactor suggest that ciprofloxacin would be deposited in different regions of the respiratory tract but predominantly in the alveolar region since most of the particles were in the range size of 4.9+/−1 μm Carrier Particles Containing PBC Nanoparticles:

Polybutylcyanoacrylate nanoparticles were spray dried in an aqueous solution containing lactose as well as in the effervescent preparation. The particle diameter of the nanoparticles was measured before and after spray drying. A t-test was performed to compare the sizes of the samples before and after spray drying. When only lactose was used, the nanoparticles had a size of 126.17+/−20.20 nm before and 259.00+/−52.70 nm after spray drying. This is a statistically significant increase in particle size at a P<0.05 value. However, using the effervescent preparations containing L-leucine and PEG 6000, the size before spray drying was 149.9+/−26.46 and the size after spray drying was 176.83+/−15.45. Here at test did not indicate a statistical difference between the nanoparticles before and after the spray drying process. This might be due to the effervescent reaction of the carrier particles, which generated forces which helped the nanoparticles to disperse more efficiently and avoid particle aggregation.

Figure 16:
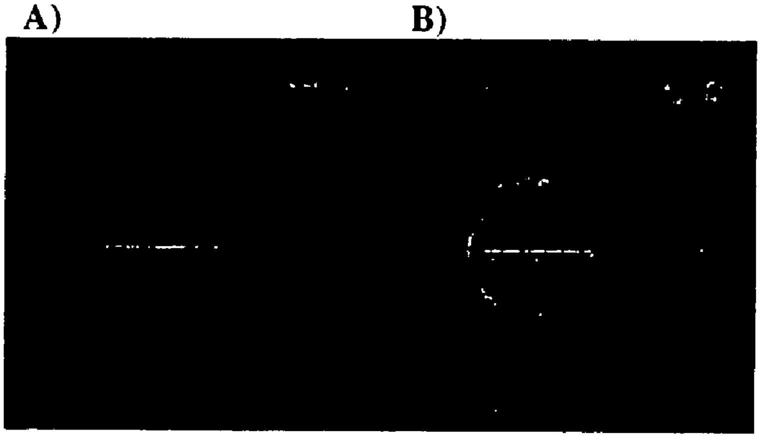
FIG. 16 shows Confocal microscopy pictures of a carrier particle. A) The red channel shows a hollow carrier particle with its matrix. B) The green channel shows the nanoparticles distributed continuously throughout the hollow carrier particle.
Figure 17:
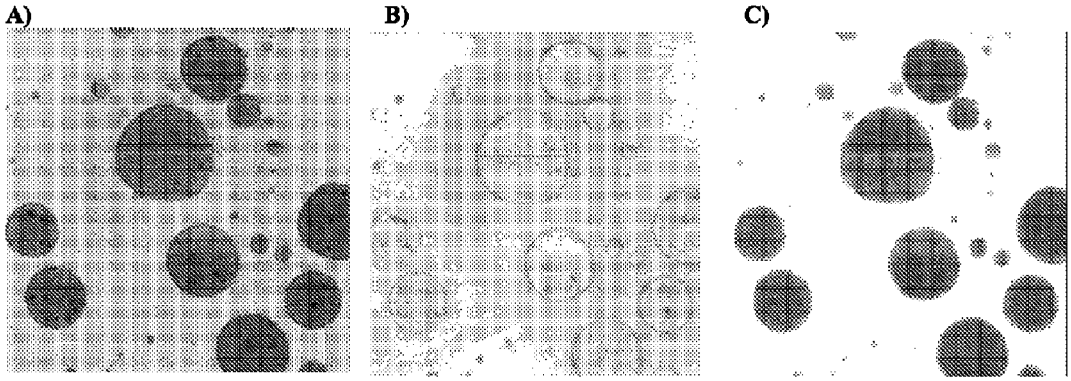
FIG. 17 shows: A) Confocal microscopy picture of effervescent particles exposed to humidity. The gas bubbles are about 30 μm in diameter. B) The green nanoparticles were actively distributed throughout the gas bubble. C) The red represents the dissolved carrier matrix.

Effervescent Properties of the Carrier Particles Containing Nanoparticles:

The effervescent properties of the carrier particles prepared using a formulation containing 4 g of lactose, 4 g of citric acid, 5 g of sodium carbonate, 20 mL of ammonia (28-30% solution), 290 mL of water, and 5 mL each of a 2.5% solution of L-leucine and 2.5% solution of PEG 6000 were observed when the carrier particles were exposed to water, aqueous surfaces or moist air. FIG. 16 shows carrier particles which were approximately 15 μm in diameter. These were hollow particles with spherical shape (FIGS. 16 A & B). The nanoparticles were distributed continuously throughout the hollow carrier particle matrix. FIG. 17 shows the swelling and dissolution of the carrier particles after exposure to humid air (FIGS. 17 A, B, and C). The matrix of the particles dissolves (red channel) while a green bubble of more than 30 μm filled with nanoparticles is visible. This proves that the nanoparticles were actively distributed throughout the gas bubble. If the particles were dispersed in water, small gas bubbles were visible immediately after dispersion.

Discussion of Results:

The present examples describe a new type of carrier particle using effervescent technology with an active release mechanism. This technology is being applied for the first time to pulmonary delivery and it is a new concept for drug delivery. An effervescent inhalable particle is different from all strategies for pulmonary delivery of active agents e.g. drugs or drug delivery systems that have been presented to date by other authors (Bosquillon C., Préat V., Vanbever R. (2004) Pulmonary delivery of growth hormone using dry powders and visualization of its local fate in rats. J. of Controlled Release. 96: 233-244; Edwards et al. (1998), supra; Steckel H., Brandes H. G. (2004) A novel spray—drying technique to produce low density particles for pulmonary delivery. International Journal of Pharmaceutics. 278: 187-95; Tsapis et al. (2002), supra; Vanbever et al. (1999), supra). This study indicates that it is possible to produce effervescent carrier particles to deliver nanoparticles or other molecules to the lungs having an appropriate mass median aerodynamic diameter.

Different powder compositions were produced in order to develop and partially optimize an effervescent aerosol carrier particle formulation. In vitro results using lactose carrier particles indicated that most of the particles will be deposited in the upper respiratory tract with minimal deposition in the lower respiratory tract. Furthermore, their shape and morphology is another indicator of heavy particles and that they are inappropriate for alveolar deposition. In order to overcome those problems, more recently many researchers have been using large porous particles or particles that contain different excipients in their formulation, such as L-leucine, albumin and dipalmitoylphosphatidylcholine (DPPC), among others. (Bosquillon et al. (2001), supra; Gliński J. et al. (2000) Surface properties of aqueous solutions of L-leucine. Biophysical Chemistry. 84: 99-103; Rabbani et al. (2005), supra). It has been shown that the addition of these components or the synthesis of large porous particles might improve the aerodynamic properties of the powders and also improve their aerolization. For these reasons, to improve particles size, the addition of L-leucine, PEG 6000 and ethanol was examined. The most pronounced effect on particle size occurred with the addition of L-leucine and PEG 6000, which improved the aerodynamic characteristics of the powder particles. The in vitro results indicated that the particles were suitable for deposition throughout the lungs, and these results are consistent with those of Example 1. The mass median aerodynamic diameter and geometric standard deviation of these formulations ranged from 2.17+/−0.42 μm and 2.00+/−0.06, respectively.

The results were in agreement with other studies (Bosquillon et al. (2001), supra; Gliński et al. (2000), supra).

Glinski et al. (2000), supra, found that when L-leucine was added to a water solution it caused a rapid decrease in the surface tension. In addition, L-leucine allows the preparation of powders with better aerolization properties. Corrigan et al. and Gilani et al. investigated the use of PEG in their formulations (Corrigan O. D., Healy A. M., Corrigan O. I. (2002) The effect of spray drying solutions of polyethylene glycol (PEG) and lactose/PEG on their physicochemical properties. International J. of Pharmaceutics 235: 193-205; Gilane K., Najafabadi A. B., Barghi M., Rafiee-Therani M. (2004) Aerolization of beclomethasone diprionate using spray dried lactose/polyethylene glycol carriers. European J. of Pharmaceutics and Biopharmaceutics. 58: 596-606). They found that polyethylene glycol had a major impact on the size and morphology of carrier particles. In addition, the presence of PEG 6000 changed the surface texture of the carrier particles from a smooth surface to a more aspirated surface. Similar effects were observed in our study using the effervescent formulation. This effect on the surface of the carrier particles can improve the amount of particles deposition in the respiratory tract, since particles with a more irregular shape tend to have a larger profile deposition than particles with a regular shape. In addition, the presence of polyethylene glycol might also influence the crystalline and polymorphic form of spray-dried lactose and presumably of incorporated drugs (Gilani et al. (2004), supra).

The effervescent effect of the carrier particles was investigated using confocal microscopy. The results clearly showed the formation of gas bubbles after the particles being exposed to humidity. The carrier particles were able to release nanoparticles with less particle agglomeration compared to carrier particles without active release. Sham et al., (2004), supra, conducted a study-using lactose carrier particles containing nanoparticles. In the cited study, it was found that some clusters of nanoparticles were observed in the carrier particles which increased the nanoparticle size after spray drying. Our results showed a significant increase in the size of the released nanoparticles when lactose alone was used as a carrier. However, when effervescent particles were used, no statistically significant difference was observed. These findings indicate that the effervescent reaction appears to improve the dispersion of the nanoparticles from the carrier particle. Similar effects were reported for effervescent atomization of pharmaceutical coatings. Here, effervescent dispersion of very small droplets was achieved with lower air-to liquid mass ratios compared to conventional spray technologies (Petersen F. J., Wørts O., Schæfer T., Sojka P. E. (2004) Design and Atomization Properties for an Inside-Out Type Effervescent Atomizer. Drug Development and Industrial Pharmacy 30 (3): 319-326).

Ciprofloxacin was used as a model drug in order to evaluate the effect of active drug release from the carrier particles compared to passive release and dissolution. Rygnestad et al., (2000) reported that effervescent paracetamol tablets were absorbed significantly faster compared to conventional tablets (Rygnestad T., Zahlsen K., F. A. Samdal F. A. (2000) Absorption of effervescent paracetamol tablets relative to ordinary paracetamol tablets in healthy volunteers. European Journal of Clinical Pharmacology 56 (2): 141-143). Dosage form disintegration and drug dissolution are typically increased when effervescent formulations are used.

It has been demonstrated that the effervescent carrier particles were able to increase the drug dissolution. The fast release of the drug was due to the effervescent reaction, and the amount of ciprofloxacin released was higher compared to the amount of ciprofloxacin found when lactose carrier particles were dissolved. Thus, this study shows that it is possible to produce carrier particles which actively release ciprofloxacin using effervescent inhalation technology. In addition, these carrier particles have the appropriate size (MMAD≦5 microns) for deep lung deposition. It is envisioned that these effervescent inhalable powders will increase the absorption and bioavailability of drugs in the lungs similarity to as described for the oral route of administration. (El-Shaboury, M. H., Abd El-Gawad, A. H., Gabr, K. E., Hashem, F. M.; Effect of effervescent salt on the dissolution and bioavailability of drugs from capsules filled on a dosator-type capsule-filling machine; Pharmazeutische Industrie, Volume 55, Issue 2, 1993, Pages 176-179).

Thus, a new effervescent formulation has been established for use in the pulmonary route of administration. The active release mechanism increased drug dissolution and enhanced the dispersion of nanoparticles over the effervescent gas bubble interface. It is envisioned that this formulation may be used to create airborne nano- or micro-droplets containing molecules or active principles in nano- or micro-meter scale. These formulations can be synthesized with an adequate particle size for deep lung deposition. Furthermore, effervescent carrier particles can be used to deliver a large range of substances to the lungs, and it is envisioned that these will present a faster release compared to others carrier particles.

Example 3

Preparation of Effervescent Inhalable Carrier Particles Containing Blank Nanoparticles and Doxorubicin-Loaded Nanoparticles by Spray Freeze-Drying, and In Vivo Studies with Effervescent Inhalable Carrier Particles Containing Nanoparticles Methods Preparation of Blank Cyanoacrylate Nanoparticles 100 μL of n-butylcyanoacrylate monomer was added to 1% dextran 70 solution in 10 mL of 0.01 M HCl under constant stirring at 600 rpm. After 4 hours the pH of the nanoparticle suspension was adjusted to 7 and filtered through 0.8 μm membrane filter (Nuclepore Track-Etch membrane, Whatman, USA). The nanoparticle suspension was kept in a refrigerator at 4° C.

Preparation of Doxorubicin Nanoparticles

100 μl of n-butylcyanoacrylate monomer was added to 1% dextran solution in 8 mL of 0.01 M HCl under constant stirring at 600 rpm. Doxorubicin hydrochloride powder 50 mg was dissolved in 2 mL of distilled water and after 40 minutes the solution was added to the reaction flask. After 4 hours the pH of the nanoparticle suspension was adjusted at 7 and filtered through 0.8 μm membrane filter (Nuclepore Track-Etch membrane, Whatman, USA). The doxorubicin-loaded nanoparticle suspension was kept in a refrigerator at 4° C.

Determination of Drug Loading on Nanoparticles

Drug loading was calculated from the difference between the initial doxorubicin concentration and the superfluous doxorubicin determined in the supernatant liquids. The drug concentration was determined using a spectrophotometer (Beckman DU 7400 spectrophotometer, CA, USA) at the maximum wavelength of 233 nm.

Particle Size Analysis of Nanoparticles

The particle size of the nanoparticles was determined by photon correlation spectroscopy using a Zetasizer, model HSA 3000 (Malvern, Worcestershire, England). For particle size analysis, 100 μL of the nanoparticle suspension was dispersed in 4 mL de-ionized water. Measurements were carried out at 25° C. The mean particle size and polydispersity index were determined.

Spray Freeze-Drying of Non-Effervescent Powder 1.2 g lactose monohydrate (FlowLac) was added to nanoparticle suspension before spray freeze-drying. A two-fluid nozzle (Spraying Systems Co., Wheaton, Ill., USA) utilizing gaseous nitrogen at a flow rate of 0.6 scfm was used to atomize the nanoparticle suspension, which was supplied at a flow rate of 37 mL/min using a peristaltic pump (CTP-A, Chem-Tech, Punta Gorda, Fla., USA). The nozzle was placed ~15 cm above a 600 mL flask containing 300-400 mL of liquid nitrogen. Following spraying, the flask contents were transferred into a Pyrex vacuum beaker, and the liquid nitrogen was allowed to evaporate. The vacuum container was attached to a freeze dry system (Labconco Corp., Kansas City, USA) operating at 0.004 mbar with the collector at −52° C. The powder in the flask was held at subzero temperature for the initial 7 hours, followed by 41 hours at 23° C. After 48 hours, the powder was collected and stored in a sealed vial at 4° C.

Preparation of Effervescent Solution 250 mg sodium carbonate and 1000 mg spray dried lactose monohydrate (FlowLac) was dissolved in 3 mL distilled water and 300 μL ammonium hydroxide (28-30%) was added. The solution was kept in a tightly closed container. Before spray freeze drying, the solution was added to 200 mg citric acid powder.

Spray Freeze-Drying of Effervescent Powder

Nanoparticle suspension was mixed with effervescent solution. The suspension was spray freeze-dried as explained above.

Measurement of Mass Median Aerodynamic Diameter

Mass median aerodynamic diameter (MMAD) of the powder was measured as previously described using a Mark II Anderson Cascade Impactor (Graseby Anderson, Smyrna, Ga., USA) with effective cut-off points recalibrated at 60 l/min. A passive dry powder inhaler that utilizes cyclonic action as well as mechanical impaction to disperse powder particles was used to deagglomerate and deliver the powder (described in U.S. Patent Application Publication No. 2004/0107963 to Finlay, W. H. & Wang, Z., filed Dec. 2, 2003, entitled "Device and Method for Deagglomeration of Powder for Inhalation", the contents of which are herein incorporated by reference). The flow rate was monitored with a pneumotachometer (PT 4719, Hans Rudolph Inc., Kansas City, Mo., USA).

In Vivo Experiments

Female 4-5 weeks old BALB/c nude mice were treated with 1 mg of effervescent powder containing blank nanoparticles over a period of 60 days. A DP-4M insufflator (Penn-Century Inc., Philadelphia, Pa., USA) was used to administer the powder. The insufflator was calibrated by weighing before and after powder filling, as well as after administration of the powder to determine precisely the delivered dose. The tip of the insufflator tube was positioned near the carina (first bifurcation) so that the measured dose of effervescent powder could penetrate deep into the lung. The average body weight and morbidity score of the mice were monitored. The morbidity score entails 5 categories of physiologic parameters monitored daily (see Table 3 below).

TABLE 3

Morbidity Scoring of Mice Treated with Inhalable Carrier Particles Containing Nanoparticles

| Project/Animal Identification: | Score. | Date/Time |
|---|---|---|
| Appearance | | |
| Normal | 0 | |
| General lack of grooming | 1 | |
| Coat staring, ocular or nasal discharge | 2 | |
| Piloerection, hunched up | 3 | |
| Body Weight | | |
| Normal <5% | 0 | |
| body wt. drop 6-15% | 1 | |
| body wt. drop 16-25% | 2 | |
| body wt. drop 26-35% | 3 | |
| body wt. drop >35% | 4 | |
| Food Intake | | |
| Normal | 0 | |
| food intake drop 10-33% | 1 | |
| food intake drop 34-75% | 2 | |
| food intake drop >75% | 3 | |
| Clinical Signs | | |
| Normal resp. rate and hydration | 0 | |
| Slight changes | 1 | |
| Resp. rates up or down 30%, measurable dehydration | 2 | |
| Resp. rates changes 50% or very low, severe dehydration | 3 | |
| Behavior | | |
| Normal | 0 | |
| Minor inactivity or exaggerated responses | 1 | |
| Moderate change in expected behavior, isolated or listless | 2 | |
| Reacts violently, or very weak and precomatose | 3 | |
| Total | | |

Humane Endpoints and Actions 0-5 Normal.

6-10 Monitor carefully, consider analgesics. Increase monitoring frequency of body weight and food intake if "2" is scored in either category.

11-15 Suffering, provide relief, observe regularly. Seek second opinion from animal care staff and Director of Animal Care as indicated. Consider termination.

Any individual score of 4, terminate animal.

Results

Figure 18:
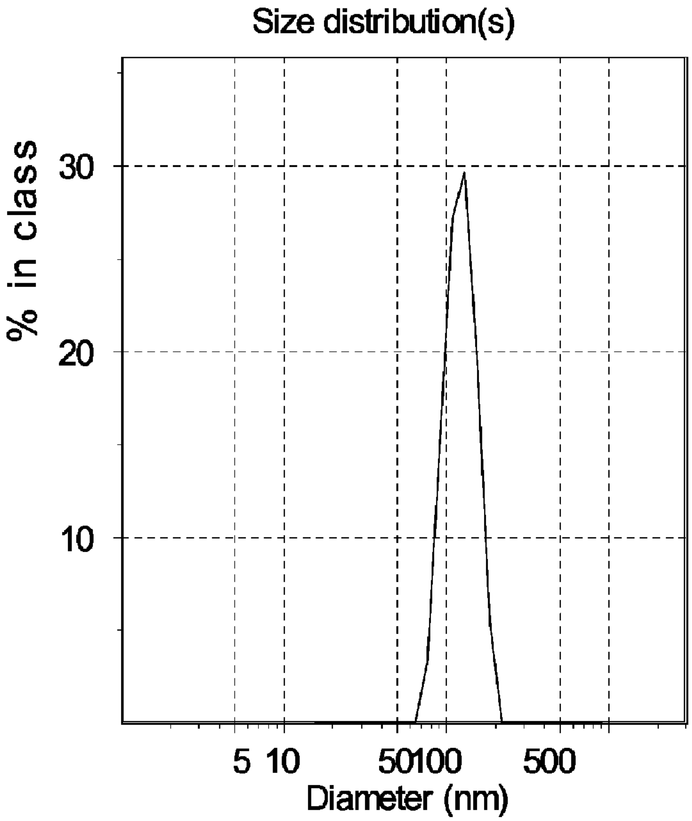
FIG. 18 illustrates the particle size distribution of doxorubicin-loaded nanoparticles prepared by the spray freeze drying process described in Example 3.

The drug loading study of the non-effervescent powder showed that approximately 85% of doxorubicin was adsorbed onto the poly(butylcyanoacrylate) nanoparticles. The loading amount of doxorubicin in the non-effervescent carrier particles after spray-freeze drying was calculated as 35 μg/mg powder. The mean particle sizes of doxorubicin-loaded nanoparticles after re-dissolving of the spray-freeze-dried non-effervescent powders were 145±20 nm (see FIG. 18). The aerodynamic particle sizes of non-effervescent carrier particles loaded with blank and doxorubicin nanoparticles were 3.45±0.11 (n=3) and 3.41±0.22 μm respectively (n=6).

The effervescent particles release gas bubbles when put into water equally to the spray dried particles.

Figure 19A:
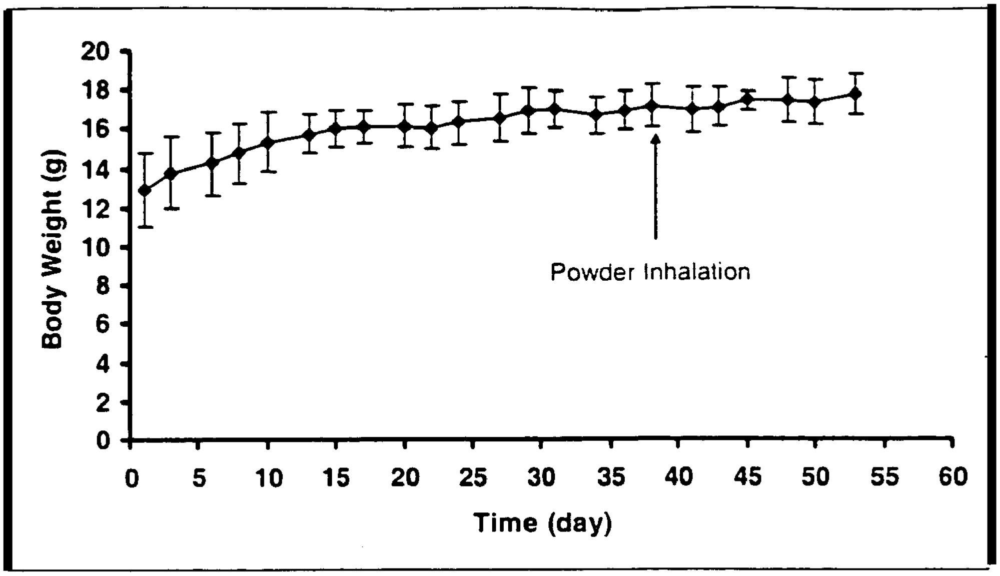
FIGS. 19*a* and 19*b* illustrate the average body weight (19*a*) and morbidity score (19*b*) of BALB/c mice treated with inhaled effervescent powder containing blank nanoparticles.
Figure 19B:
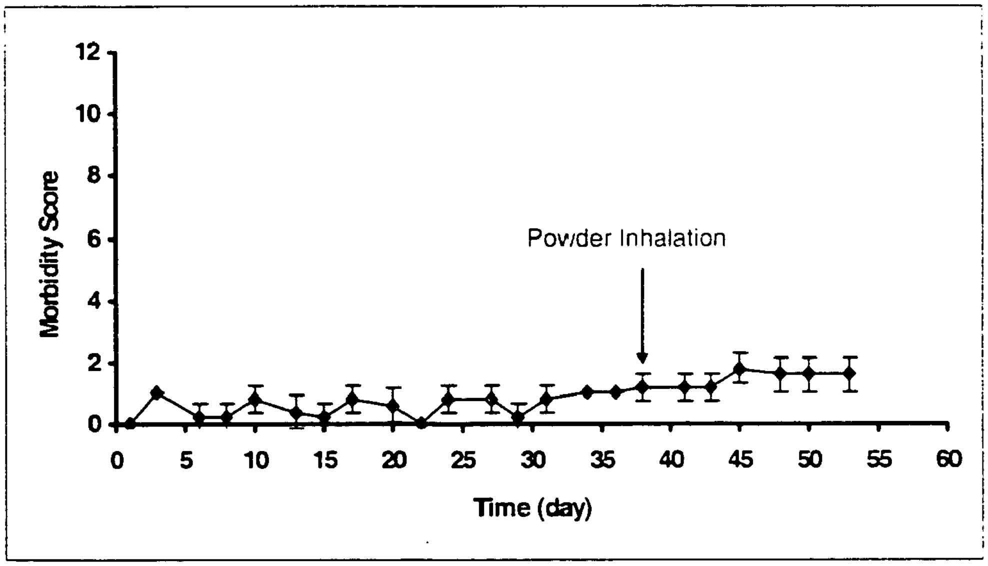

Female 4-5 weeks old BALB/c nude mice were able to inhale the effervescent particles without harm using a DP-4M insufflator (Penn-Century Inc., Philadelphia, Pa., USA) FIGS. 19*a* and 19*b* illustrate the average body weight (19*a*) and morbidity score (19*b*) of BALB/c mice treated with inhaled effervescent powder containing blank nanoparticles. The effervescent powder is well tolerated as shown by these mice over this time course.

The present invention has been described with reference to specific embodiments. Various modifications of the invention in addition to those shown and described herein apparent to those skilled in the art from the preceding description are considered to fall within the scope of the appended claims. Every reference cited herein is hereby incorporated by reference in its entirety.

The invention claimed is:

1. A method of preparing an effervescent powder suitable for nasal, bronchial, or pulmonary administration, said method comprising: (i) preparing a formulation comprising an inorganic or organic carbonate, an acid, and aqueous ammonia, wherein minimal reaction occurs between the inorganic or organic carbonate and the acid; (ii) forming the formulation of step (i) into particles having a mass median aerodynamic diameter suitable for nasal, bronchial, or pulmonary administration by inhalation.

2. The method of claim 1, wherein the formulation further comprises an inorganic or organic bicarbonate.

3. The method of claim 2, wherein the inorganic bicarbonate is sodium bicarbonate.

4. The method of claim 1, wherein the inorganic carbonate is sodium carbonate and the acid is citric acid.

5. The method of claim 1, wherein the formulation further comprises one or more inert filler materials.

6. The method of claim 5, wherein the one or more inert filler materials are selected from the group comprising lactose and mannitol.

7. The method of claim 1, wherein the particles further comprise one or more lubricants.

8. The method of claim 7, wherein the lubricants are polyethylene glycol and/or L-leucine.

9. The method of claim 1, wherein the particles further comprise an active agent and the particles act as a carrier for the active agent.

10. The method of claim 9, wherein the active agent is an antibiotic.

11. The method of claim 10, wherein the antibiotic is ciprofloxacin.

12. The method of claim 9, wherein the active agent comprises nanoparticles.

13. The method of claim 12, wherein the nanoparticles are loaded with an anticancer agent.

14. The method of claim 13, wherein the anticancer agent is doxorubicin.

15. The method of claim 1, wherein the mass median aerodynamic diameter is less than or equal to 5.0 μm and the powder is for pulmonary administration.

16. The method of claim 1, wherein the mass median aerodynamic diameter is more than 5.0 μm and the powder is for nasal or bronchial administration.

17. The method of claim 1, wherein the formulation is formed into particles by spray freeze-drying.

18. The method of claim 1, wherein the formulation is formed into particles by spray drying.

* * * * *